(12) United States Patent
Shelchuk

(10) Patent No.: US 7,245,967 B1
(45) Date of Patent: Jul. 17, 2007

(54) PARASYMPATHETIC NERVE STIMULATION FOR TERMINATION OF SUPRAVENTRICULAR ARRHYTHMIAS

(75) Inventor: Anne M. Shelchuk, San Rafael, CA (US)

(73) Assignee: Pacesetter, Inc., Sylmar, CA (US)

( * ) Notice: Subject to any disclaimer, the term of this patent is extended or adjusted under 35 U.S.C. 154(b) by 557 days.

(21) Appl. No.: 10/460,149

(22) Filed: Jun. 11, 2003

Related U.S. Application Data

(60) Provisional application No. 60/389,053, filed on Jun. 12, 2002, provisional application No. 60/388,784, filed on Jun. 12, 2002, provisional application No. 60/388,709, filed on Jun. 12, 2002, provisional application No. 60/388,707, filed on Jun. 12, 2002, provisional application No. 60/388,623, filed on Jun. 12, 2002.

(51) Int. Cl.
*A61N 1/05* (2006.01)
*A61N 1/36* (2006.01)

(52) U.S. Cl. .................. 607/14; 607/122; 607/129

(58) Field of Classification Search .............. 607/4, 607/9, 14, 20, 27–28, 122–123, 129; 600/515, 600/518, 521
See application file for complete search history.

(56) References Cited

U.S. PATENT DOCUMENTS

| | | | | |
|---|---|---|---|---|
| 4,712,555 A | 12/1987 | Thornander et al. | ......... | 128/419 |
| 4,788,980 A | 12/1988 | Mann et al. | ......... | 128/419 |
| 4,940,052 A | 7/1990 | Mann et al. | ......... | 128/419 |
| 4,944,298 A | 7/1990 | Sholder | ......... | 128/419 |
| 5,024,222 A | 6/1991 | Thacker | ......... | 128/419 PG |
| 5,193,535 A | 3/1993 | Bardy et al. | ......... | 128/419 D |
| 5,199,428 A | 4/1993 | Obel et al. | ......... | 128/419 |
| 5,203,326 A | 4/1993 | Collins | ......... | 128/419 PG |
| 5,243,980 A | 9/1993 | Mehra | ......... | 607/6 |
| 5,330,507 A | 7/1994 | Schwartz | ......... | 607/14 |
| 5,330,508 A | 7/1994 | Gunderson | ......... | 607/14 |
| 5,334,221 A | 8/1994 | Bardy | ......... | 607/14 |
| 5,356,425 A * | 10/1994 | Bardy et al. | ......... | 607/14 |
| 5,466,245 A | 11/1995 | Spinelli et al. | ......... | 607/17 |
| 5,466,254 A | 11/1995 | Helland | ......... | 607/123 |
| 5,476,483 A | 12/1995 | Bornzin et al. | ......... | 607/17 |
| 5,507,784 A | 4/1996 | Hill et al. | ......... | 607/14 |
| 5,522,854 A | 6/1996 | Ideker et al. | ......... | 607/6 |
| 5,549,655 A | 8/1996 | Erickson | ......... | 607/42 |
| 5,620,468 A * | 4/1997 | Mongeon et al. | ......... | 607/5 |
| 5,700,282 A | 12/1997 | Zabara | ......... | 607/6 |
| 5,720,295 A * | 2/1998 | Greenhut et al. | ......... | 600/517 |

(Continued)

FOREIGN PATENT DOCUMENTS

EP     0 547 734 A2     6/1993

(Continued)

OTHER PUBLICATIONS

Mendelowitz, "Advances in Parasympathetic Control of Heart Rate and Cardiac Function," News Physio. Sci., 1999; 14:155-161.

(Continued)

*Primary Examiner*—Carl Layno
*Assistant Examiner*—Jessica L. Reidel

(57) ABSTRACT

Terminating supraventricular arrhythmias through parasympathetic nerve stimulation. The method comprises detecting a supraventricular arrhythmia, stimulating a parasympathetic nerve and determining whether the supraventricular arrhythmia terminated or worsened. Various exemplary methods include delivering one or more stimulation pulses during postinspiration and/or in response to one or more cardiac events.

37 Claims, 16 Drawing Sheets

U.S. PATENT DOCUMENTS

| | | | |
|---|---|---|---|
| 5,836,974 A | 11/1998 | Christini et al. | 607/5 |
| 5,836,976 A | 11/1998 | Min et al. | 607/6 |
| 6,006,134 A | 12/1999 | Hill et al. | 607/9 |
| 6,134,470 A * | 10/2000 | Hartlaub | 607/14 |
| 6,141,590 A * | 10/2000 | Renirie et al. | 607/20 |
| 6,272,377 B1 | 8/2001 | Sweeney et al. | 600/515 |
| 6,314,323 B1 | 11/2001 | Ekwall | 607/23 |
| 6,449,503 B1 | 9/2002 | Hsu | 600/518 |
| 6,473,644 B1 | 10/2002 | Terry, Jr. et al. | 607/2 |
| 6,611,713 B2 | 8/2003 | Schauerte | 607/14 |
| 6,687,540 B2 | 2/2004 | Marcovecchio | 607/5 |
| 6,690,971 B2 * | 2/2004 | Schauerte et al. | 607/17 |
| RE38,654 E | 11/2004 | Hill et al. | 607/9 |
| 6,876,880 B2 * | 4/2005 | Hess et al. | 607/14 |
| 6,889,079 B2 | 5/2005 | Bocek et al. | 607/9 |
| 2003/0040774 A1 | 2/2003 | Terry, Jr. et al. | 607/2 |
| 2003/0078623 A1 * | 4/2003 | Weinberg et al. | 607/9 |
| 2004/0230252 A1 | 11/2004 | Kullok et al. | 607/48 |
| 2005/0267542 A1 | 12/2005 | David et al. | 607/17 |

FOREIGN PATENT DOCUMENTS

| | | |
|---|---|---|
| EP | 0 547 734 A3 | 6/1993 |
| EP | 0 547 734 B1 | 6/1993 |
| EP | 0 688 577 A1 * | 12/1995 |
| EP | 1 106 206 A2 | 6/2001 |
| EP | 1 304 135 A2 | 4/2003 |
| EP | 1 304 135 A3 | 4/2003 |

OTHER PUBLICATIONS

Pauza et al., "Morphology, Distribution, and Variability of the Epicardiac Neural Ganglionated Subplexuses in the Human Heart", Anatomical Record, 2000; 259:353-382.

Kawada et al., "Vagosympathetic Interactions in Ischemia-Induced Myocardial Norepinephrine and Acetylcholine Release," Am. J. Physiol Heart Circ. Physiol., 2001; 280:H216-H221.

Wen et al., "Electrophysiological Mechanisms and Determinants of Vagal Maneuvers for Termination of Paroxysmal Supraventricular Tachycardia," Circulation, 1998; 98:2716-2723.

Olguin et al., "Heterogeneous Atrial Denervation Creates Substrate for Sustained Atrial Fibrillation," Circulation, 1998; 98:2608-2614.

Rahme et al., "Effect of Autonomic Neurotransmitters on Excitable Gap Composition in Canine Atrial Flutter," Cam. J. Physiol., Pharm., 2001; 79:13-17.

Ringdahl, "Vagally Mediated Atrial Fibrillation in a Young Man," Arch Fam. Med., 2000; 9:389-390.

Schlepper, "Einflüsse des Autonomen Nervensystems bei Supraventrikulären Rhythmusstörungen," Z. Kardiol., 1986; 75, Suppl. 5:35-40.

Burger et al., "Comparison of the Occurrence of Ventricular Arrhythmias in Patients with Acutely Decompensated Congestive Heart Failure Receiving Dobutamine Versus Nesiritide Therapy," Am. J. Cardiol., 2001; 88:35-39.

Levett et al., "Cardiac Augmentation can be Maintained by Continuous Exposure of Intrinsic Cardiac neurons to a β-Adrenergic Agonist or Angiotensin II," J. Surg. Research, 1996; 66:167-173.

Wallick et al., "Separate Parasympathetic Control of Heart Rate and Atrioventricular Conduction of Dogs," Am. Phys. Society, 1990; 259(28):H536-H542.

Mazgalev et al., "Autonomic Modification of the Atrioventricular Node During Atrial Fibrillation Role in the Slowing of Ventricular Rate," Circulation, 1999; 99:2806-2814.

Chen et al., "Intracardiac Stimulation of Human Parasympathetic Nerve Fibers Induces Negative Dromotropic Effects: Implication with the Lesions of Radiofrequency Catheter Ablation," J. Cardiovasc. Electrophysiol., Mar. 1998; vol. 9, No. 3: 245-252.

Lazzara et al., "Selective in Situ Parasympathetic Control of the Canine Sinoatrial and Strioventricular Nodes," Circulation Research, Mar. 1973, vol. XXXII:393-401.

Schauerte et al., "Ventricular Rate Control During Atrial Fibrillation by Cardiac Parasympathetic Nerve Stimulation: a Transvenous Approach," J. Am. College of Cardiology, 1999; vol. 34, No. 7:2043-2050.

Waninger et al., "Characterization of Atrioventricular Nodal Response to Electrical Left Vagal Stimulation," Annals of Biomedical Eng, 1999; vol. 27:758-762.

Kulboka et al., "Changes of Heart Electrophysiological Parameters After Destruction of Epicardial Subplexuses that Innervate Sinoatrial Node," Medicina, 2003; 39 Tomas, No. 6: 589-595.

Cao, Ji-Min MD et al., "Relationship Between Regional Cardiac Hyperinnervation and Ventricular Arrhythmia," CIRCULATION. 2000; 101:1960-1969.

Cohn, Jay N. MD, Preventing Congestive Heart Failure, American Family Physician, vol. 57, No. 8 (Apr. 15, 1998), pp. 1901-1904.

Du, Xiao-Jun et al., "Response to cardiac sympathetic activation in transgenic mice overexpressing β2-adrenergic receptor," American Physiological Society (1996), pp. H630-H636.

Eisenhofer, Graeme PhD et al., "Cardiac Sympathetic Nerve Function in Congestive Heart Failure," CIRCULATION, 1996;93:1667-1676.

Frantz, Robert P. MD, "Beta blockade in patients with congestive heart failure," Postgraduate Medicine, vol. 108, No. 3 (Sep. 1, 2000), pp. 108-118.

Gomberg-Maitland, Mardi MD et al., "Treatment of Congestive Heart Failure," Arch Intern Med. 2001;161:342-352.

Grassi, Guido MD et al., "Sympathetic Activation and Loss of Reflex Sympathetic Control in Mild Congestive Heart Failure," CIRCULATION. 1995;92:3206-3211.

Kawada, Toru et al., "Vagosympathetic interactions in ischemia-induced myocardial norepinephrine and acetylcholine release," Am J Physiol Heart Circ Physiol. 280:H216-H221, 2001.

Kirchheim, H.R. et al., "Physiology and pathophysiology of baroreceptor function and neuro-hormonal abnormalities in heart failure," Basic Res Cardiol 93;Suppl 1, 1-22 (1998).

Kirchner, A. MD et al., "Left vagus nerve stimulation suppresses experimentally induced pain," NEUROLOGY 2000;55:1167-1171.

Krum, H, "Sympathetic activation and the role of beta-blockers in chronic heart failure," Aust NZ J Med 1999; 29:418-427.

Levett, J.M. MD et al. "Cardiac Augmentation Can Be Maintained by Continuous Exposure of Intrinsic Cardiac Neurons to a β-Adrenergic Agonist or Angiotensin II,", Journal of Surgical Research 66, 167-173 (1996).

Loh, Evan MD, "Overview: Old and New Controversies in the Treatment of Advanced Congestive Heart Failure," Journal of Cardiac Failure, vol. 7, No. 2 Supp. 1 (2001), pp. 1-7.

Mazgalev, Todor N. PhD et al., "Anatomic-Electrophysiological Correlations Concerning the Pathways for Atrioventricular Conduction," CIRCULATION. 20019;103:2660-2667.

Mizeres, Nicholas James, "The Cardiac Plexus in Man," The American Journal of Anatomy, vol. 112, (Jan. Mar. May 1963), pp. 141-151.

Murakami, Masahiko MD et al., "Effects of Cardiac Sympathetic Nerve Stimulation on the Left Ventricular End-Systolic Pressure-Volume Relationship and Plasma Norepinephrine Dynamics in Dogs," JPN Circ J 1997; 61:864-871.

Murakawa, Yuji MD et al., "Effect of Cervical Vagal Nerve Stimulation on Defibrillation Energy—A Possible Adjunct to Efficient Defibrillation," JPN Heart J 2003;44:91-100.

Paya, Rafael MD et al., "Changes in Canine Ventricular Refractoriness Induced by Trains of Subthreshold High-frequency Stimuli," Journal of Electrocardiology, vol. 24, No. 1 (Jan. 1991), pp. 63-69.

Shakar, Simon F. MD et al., "Low-Level Inotropic Stimulation with type III Phosphodiesterase Inhibitors in Patients with Advanced Symptomatic chronic Heart Failure Receiving β-blocking Agents," Current Cardiology Reports 2001; 3:224-231.

Shamsham, Fadi MD et al., "Essentials of the Diagnosis of Heart Failure," AM FAM Physician 2000;61:1319-28.

Sokolovas, V et al., "*Surgical Parasympathetic AV node Denervation in a Canine Model: Anatomical and Electrophysiological Studies*," HEARTWEB, vol. 2, No. 1 (Nov. 1996), pp. 1-8. http://www.heartweb.org/heartweb/1196/ep0007.htm.

Olgin, Jeffrey E. MD et al., "Hetergeneous Atrial Denervation Creates Substrate for Sustained Atrial Fibrillation," Circulation. 1998;98: 2608-2614.

* cited by examiner

PARASYMPATHETIC NERVE STIMULATION FOR TERMINATION OF SUPRAVENTRICULAR ARRHYTHMIAS

PRIORITY CLAIM AND CROSS-REFERENCE TO RELATED APPLICATIONS

The instant application claims priority to U.S. Provisional Applications: 1) Ser. No. 60/388,784, filed Jun. 12, 2002, entitled "Parasympathetic Nerve Stimulation for Supraventricular Arrhythmias," to Shelchuk; 2) Ser. No. 60/388,709, filed Jun. 12, 2002; 3) Ser. No. 60/389,053, filed Jun. 12, 2002; 4) Ser. No. 60/388,623, filed Jun. 12, 2002; 5) 60/388,707, filed Jun. 12, 2002; and 6) nonprovisional U.S. application Ser. No. 10/420,998, filed Apr. 21, 2003, entitled "Parasympathetic Nerve Stimulation for ICD and/or ATP Patients," to Shelchuk; all above applications are incorporated by reference herein.

The instant application is related to co-pending U.S. patent application having Ser. No. 10/460,013, filed Jun. 11, 2003, entitled "Vagal stimulation for improving cardiac function in heart failure or CHF patients," to Shelchuk, which is incorporated by reference herein and which claims priority to a U.S. Provisional Application having Ser. No. 60/388,709, filed Jun. 12, 2002, which is also incorporated by reference herein.

The instant application is related to co-pending U.S. patent application having Ser. No. 10/460,145, filed Jun. 11, 2003, entitled "Parasympathetic Nerve Stimulation for Control of AV Conduction," to Shelchuk, Bornzin and Falkenberg, which is incorporated by reference herein and which claims priority to a U.S. Provisional Application having Ser. No. 60/389,053, filed Jun. 12, 2002, which is also incorporated by reference herein.

The instant application is related to U.S. patent application having Ser. No. 10/460,596, filed Jun. 11, 2003, entitled "Arrhythmia Discrimination," to Shelchuk, now U.S. Pat. No. 7,139,607 and which is incorporated by reference herein and which claims priority to a U.S. Provisional Application having Ser. No. 60/388,623, filed Jun. 12, 2002, which is also incorporated by reference herein.

TECHNICAL FIELD

Exemplary methods and/or devices presented herein generally relate to cardiac pacing and/or stimulation therapy. Various exemplary methods and/or devices concern stimulating parasympathetic nerves in a patient subject to certain supraventricular arrhythmias.

BACKGROUND

Supraventricular arrhythmias (SVAs) are characterized by abnormal rhythms that arise in the atria or the atrioventricular node (AV node), essentially arising in any tissue located anatomically above the ventricles. An SVA can exhibit heart rates between approximately 140 beats per minute (bpm) and approximately 250 bpm. The most common SVAs are atrial flutter and atrial fibrillation. Many SVAs involve the AV node, for example, AV nodal reentry tachycardia (AVNRT) where the arrhythmia repeatedly re-excites tissue via reentrant pathway through the AV node.

Atrial flutter can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation. Fibrillation commonly occurs in conjunction with atrial enlargement associated with heart disease. Fibrillation can however, also occur in the absence of any apparent heart disease. In fibrillation, the atrial rate can increase to more than 350 bpm and cause the atria to fail to pump blood effectively. Under such circumstances, the ventricular beat may also become haphazard, producing a rapid irregular pulse. Although atrial fibrillation may cause the heart to lose approximately 20 to 30 percent of its pumping effectiveness, the volume of blood pumped by the ventricles usually remains within the margin of safety, again because the atrioventricular node blocks out many of the chaotic beats. Hence, during atrial fibrillation, the ventricles may contract at a lesser rate than the atria, for example, of approximately 125 bpm to approximately 175 bpm.

Various studies have reported on interactions between the autonomic nervous system and SVAs. For example, Schlepper, "Effects of the autonomic nervous system in supraventricular arrhythmia", Z. Kardiol., 75, Suppl. 5: 35–40 (1986), original text in German, reported that "influences of the autonomic nervous system may cause modifications of the initiation, continuation and discontinuation of supraventricular rhythm disturbances". In particular, Schlepper reported that "in atrial fibrillation and atrial flutter the influence of the autonomic nervous system is apparent in a form of the vagotonically and sympathotonically evoked paroxysms". Indeed, a study by Ringdahl, "Vagally mediated atrial fibrillation in a young man," Arch. Fam. Med., 9:389–390 (2000), recognized that atrial fibrillation may be parasympathetically or sympathetically mediated. Ringdahl reported that sympathetic effects are common in middle-aged and elderly patients with underlying heart disease while, in the young, where heart disease is typically not present, vagal influences are more likely to predominate. Hence, for patients diagnosed with heart disease, increased sympathetic tone is a likely factor in arrhythmia initiation.

While the Ringdahl study indicates that both autonomic branches can play a role in initiating arrhythmia (the responsible branch determined largely by patient age and disease state), both branches may also play a role in terminating arrhythmia. Perhaps the simplest approach to termination of an SVA through parasympathetic stimulation involves Valsalva's maneuver. Valsalva's maneuver involves having a patient (i) inhale and hold her breath, (ii) bear down while holding her breath, as if to have a bowel movement, and (iii) hold the position for approximately 20 seconds to approximately 30 seconds. This maneuver aims to terminate a SVA by increasing parasympathetic tone and consequently slow conduction through the AV node. Another technique involves application of pressure to the carotid sinuses. For example, a physician may apply gentle and steady pressure over a patient's right carotid sinus and hold for approximately 5 to approximately 10 seconds. If a favorable response does not results from application of pressure to the right carotid sinus, then after a short wait (e.g., approximately 2 to 4 minutes), the technique may be applied to the left carotid sinus.

In general, studies show that parasympathetic stimulation can terminate SVAs. However, SVA termination therapies that rely on parasympathetic stimulation have not been implemented using implantable delivery technology. Therefore, a need exists for methods and/or devices that can stimulate parasympathetic pathways to treat SVAs. In particular, a need exists for termination of sympathetically mediated SVAs via parasympathetic stimulation.

SUMMARY

Exemplary methods include those aimed at terminating supraventricular arrhythmias through parasympathetic nerve stimulation. An exemplary method includes detecting a supraventricular arrhythmia, stimulating a parasympathetic nerve and determining whether the supraventricular arrhythmia terminated or worsened. Various exemplary methods include delivering one or more stimulation pulses during postinspiration and/or in response to one or more cardiac events.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
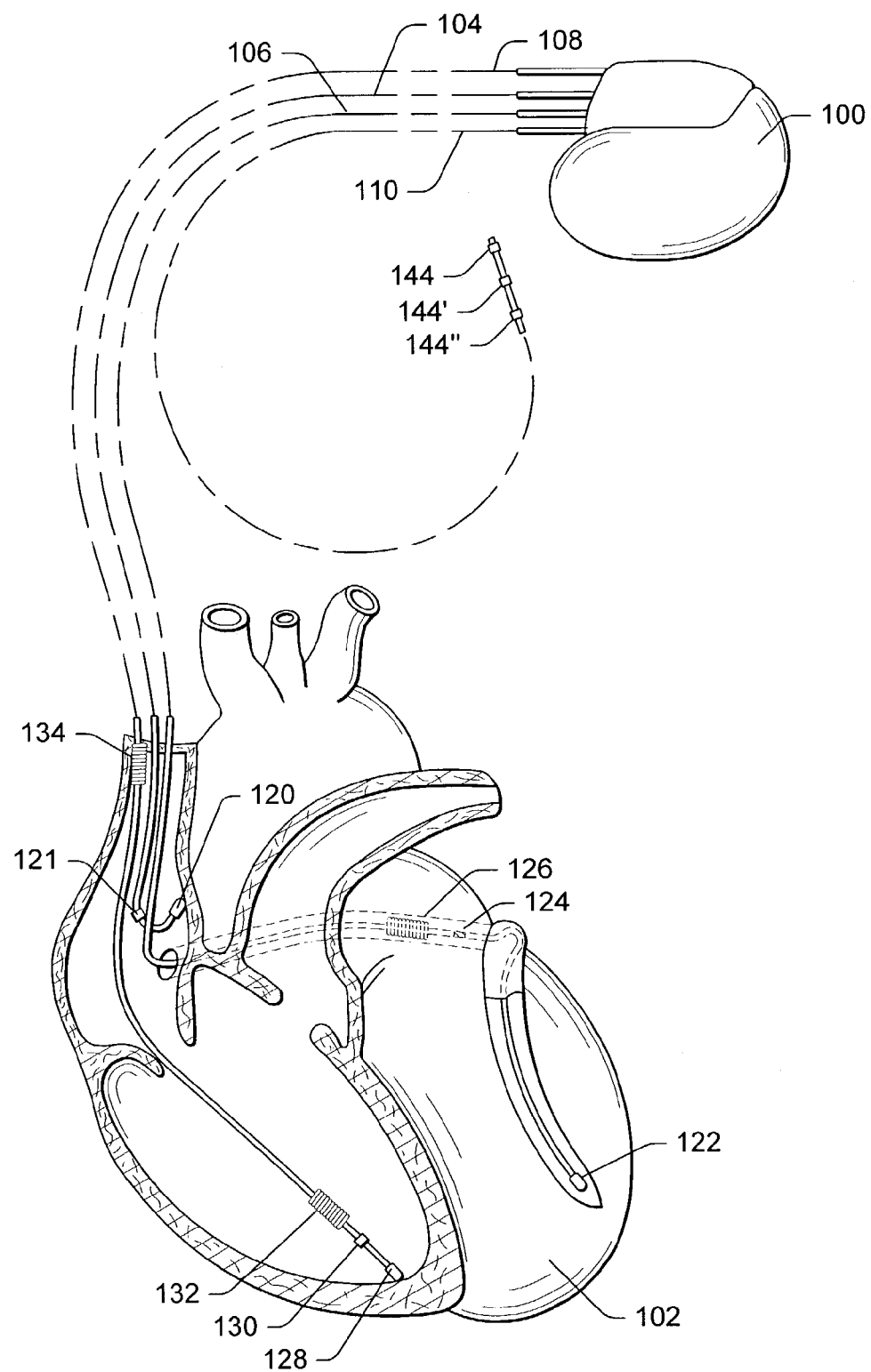
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multichamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
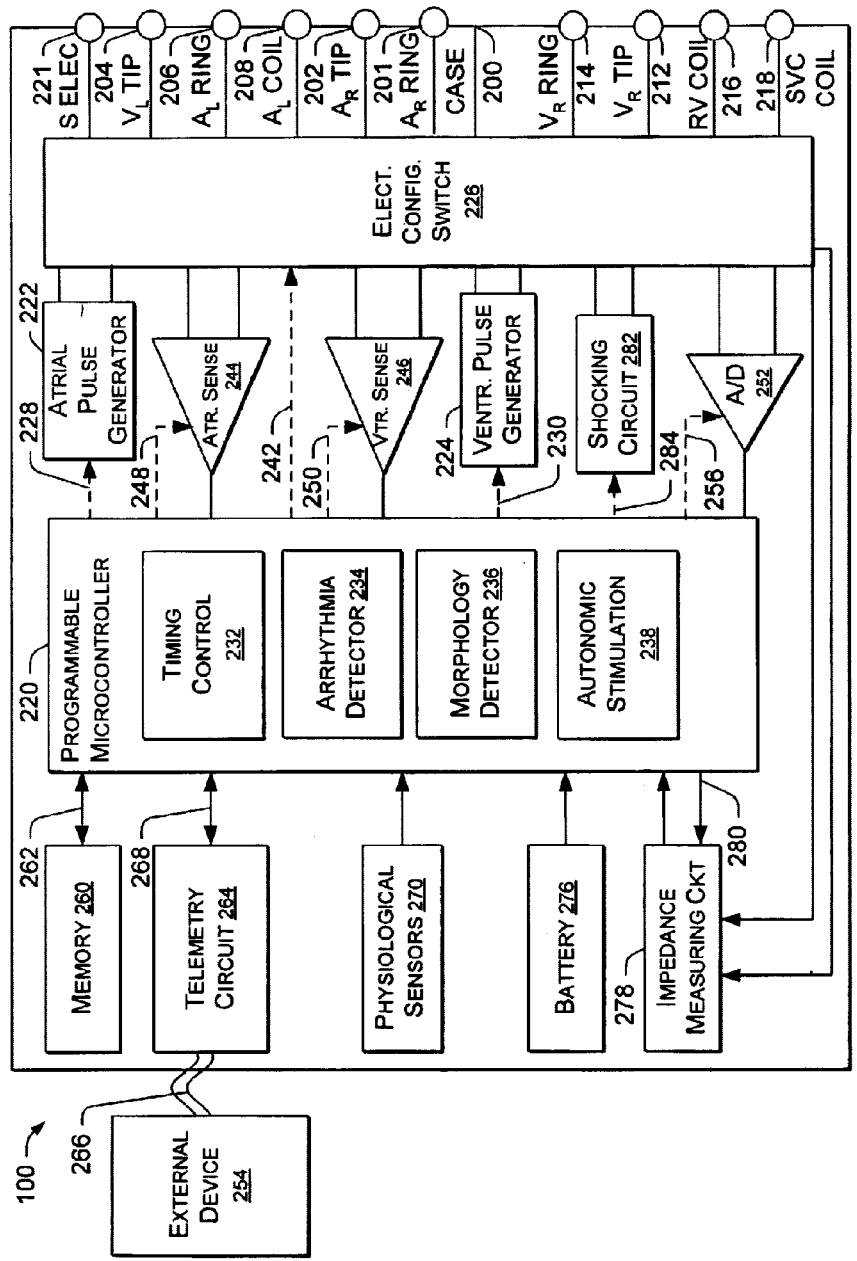
FIG. 2 is a functional block diagram of an exemplary implantable stimulation device illustrating basic elements that are configured to provide cardioversion, defibrillation, pacing stimulation and/or autonomic nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled, for example, to the right atrial lead 104, the coronary sinus lead 106, and/or the right ventricular lead 108 through the switch 226 to sample signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Supraventricular Arrhythmias (SVAs)

As already mentioned in the Background section, SVAs are characterized by abnormal rhythms that may arise in the atria or the AV node and include paroxysmal SVA, chronic SVA, atrial flutter, atrial fibrillation, AVNRT (where an electrical loop or circuit includes the AV node), etc. As described herein, various exemplary methods and/or exemplary devices are suitable for treating and/or preventing SVAs.

Many SVAs involve "reentry", a scenario in which an electrical impulse repeatedly excites tissue. Reentry may be the underlying cause of premature atrial depolarizations, supraventricular tachycardias, ventricular tachycardias and other arrhythmias. In reentry tachycardia, a cardiac impulse may reexcite a region through which it has just traveled. Some reentry loops are very large. Others are within a small area of tissue.

To more fully appreciate SVAs, especially reentrant SVAs that involve the AV node, a general description of the AV node is helpful. The AV node is situated in the inferomedial right atrium, has an endocardial location in the right atrial septum and is anterior and superior to the coronary sinus. Approximately 80% to approximately 90% of the AV nodal blood supply is from the right coronary artery while a majority of the remainder is from the circumflex artery. The AV node forms part of the only "normal" electrical connection between atria and ventricles. Specialized cells in the AV node transmit impulses very slowly requiring approximately 60 ms to approximately 130 ms to traverse about 1 cm of node tissue. In general, slowing of an impulse by AV nodal tissue protects the ventricles by typically not allowing all impulses through, which, in turn, prevents the ventricles from racing in response to a rapid atrial rhythm. Under some circumstances, the AV node blocks all impulses. As described in detail below, the AV node is profoundly influenced by autonomic tone.

An atrial flutter SVA can involve reentry with an excitable gap circulating, for example, around an anatomically defined circuit in the right atrium. Further, SVAs may include multiple reentry wavefronts. In general, wavefronts are affected by tissue mass, conduction velocity and ERP. As already mentioned, SVAs can involve AV node reentry; however, sinus node reentry is also possible, wherein a reentrant circuit forms in and/or around the sinus node. A reentrant circuit may also be intra-atrial, wherein a circuit includes the right and left atria. Regarding a reentrant circuit that includes the AV node, a dissociation of the AV node may occur wherein fast and slow pathways result.

SVAs that include reentrant circuits may also include tissue such as that associated with veins and/or venous structures. For example, the muscular sheath of the coronary sinus may act as a pathway for a reentrant circuit and may also stabilize circuits that utilize the isthmus near the inferior vena cava. Further, an SVA may originate at a focus on and/or near a pulmonary vein. Scar tissue may also dictate circuit geometry.

In general, atrial fibrillation is usually due to reentrant excitation within the atria with multiple reentry circuits; atrial flutter usually begins with a premature beat and may be supported with a reentry mechanism or a single ectopic focus; and supraventricular tachycardia, or atrial tachycardia, is usually a normal morphology tachycardia which is not driven by the SA node.

Acetylcholine Lengthens Excitable Gap

A feature of reentrant arrhythmias is a region definable as an excitable gap, i.e., a region that has partially or fully recovered its excitability or ability to depolarize. The excitable gap is, in part, determined by the size of the reentry circuit and the electrophysiological properties of its tissue components. However, external influences may also significantly modify characteristics of an excitable gap. A study by Rahme et al., "Effect of autonomic neurotransmitters on excitable gap composition in canine atrial flutter", *Can. J. Physiol. Pharmacol.*, 79:13–17 (2001), reported on how parasympathetic and sympathetic neuroeffectors can influence an excitable gap. In general, the neuroeffector acetylcholine shortens atrial refractory period while the neuroeffector norepinephrine shortens atrial refractory period and increases dispersion, which can facilitate induction of atrial fibrillation, etc. Thus, overall, while both acetylcholine and norepinephrine shortened atrial flutter cycle length (from approximately 134 ms to approximately 117 ms and approximately 125 ms, respectively), they also significantly increased the length of the excitable gap (from approximately 27 ms to approximately 34 ms and approximately 50 ms, respectively). Note that acetylcholine increased the excitable gap by approximately 23 ms compared to only approximately 7 ms for norepinephrine. Acetylcholine also effected atrial effective refractory period more than norepinephrine (from approximately 107 ms to approximately 67 ms and approximately 91 ms, respectively). Rahme et al., concluded that "vagal stimulation in particular can promote the continued circulation of the wavefront during AFl [atrial flutter]". However, as noted below, an increase in the length of an excitable gap allows for a greater probability of disruption of a circuit, for example, through anti-tachycardia pacing.

Parasympathetic Stimulation Affects AV Node and/or SA Node

Autonomic neuroeffectors may also influence reentrant circuits by influencing operation of AV and/or SA nodes. Regarding the AV node, a study by Mazgalev et al., "Autonomic modification of the atrioventricular node during atrial fibrillation: role in the slowing of ventricular rate", *Circulation*, 99:2806–2814 (1999), reported that "postganglionic vagal stimulation (PGVS) by short bursts of subthreshold current evokes release of acetylcholine from myocardial nerve terminals" and that "PGVS applied to the atrioventricular node slows nodal conduction". Overall, Mazgalev et al., recognized various attempts at AV node modification (to slow ventricular rate while preserving AV nodal function), noted "inconsistent success rates among investigators", and stated "if this [AV node modification] is unsuccessful, complete AV node destruction can be performed, rendering the patient pacemaker-dependent and undesirably altering the normal sequence of ventricular activation". The goals elaborated by Mazgalev et al., were specifically directed to slowing ventricular rate during atrial fibrillation. As described herein, various exemplary methods and/or devices optionally include parasympathetic stimulation to affect the AV node and/or AV nodal region to terminate SVAs. In particular, such exemplary methods and/or devices are suitable for terminating SVAs having reentrant circuits that involve the AV node and/or AV nodal region.

Regarding the SA node, a study by Wallick et al., "Separate parasympathetic control of heart rate and atrioventricular conduction of dogs", *Am J. Physiol.*, 259(2 Pt 2):H536–42 (1990), reported delivery of stimulation pulses to "the right pulmonary vein fat pad", which "contains parasympathetic ganglia that innervate the sinoatrial node", and "elicited a biomodal increase in the cardiac cycle length without eliciting a significant change in atrioventricular conduction time". The study by Wallick et al., also noted that the "inferior vena cava-inferior left atrial fat pad . . . contains nerves that innervate the AV node" and that stimulation of this "fat pad" elicited "a bimodal increase in the atrioventricular conduction time without eliciting any change in the cardiac cycle length". Further, Wallick et al., noted that stimulation of cervical vagi elicited an increase in cardiac cycle length "that was similar to the response we observed when the right pulmonary fat pad was stimulated". However, Wallick et al., also noted that they "found an occasional increase in AV conduction time in response to RPV fat pad stimulation", which may be due to "preganglionic fibers that synapse with the parasympathetic ganglia in the IVC-ILA fat pad also pass through or come within close proximity to the RPV fat pad". As described herein, various exemplary methods and/or devices optionally include stimulation of parasympathetic nerves to affect SA node, SA nodal region, AV node and/or AV nodal regions to terminate SVAs. In addition, when warranted, stimulation sites are optionally selected to reduce risk of parasympathetic affects on both SA and AV nodes.

Parasympathetic Stimulation for Remodeling Atrial Landscape

A study by Olgin et al., "Heterogeneous atrial dennervation creates substrate for sustained atrial fibrillation", *Circulation*, 98:2608–2614 (1998), reported that "heterogeneous electrophysiological properties, which may be due in part to autonomic innervation, are important in the maintenance of atrial fibrillation". In particular, Olgin et al., noted that "regional denervation resulted in an increased dispersion of refractoriness that facilitated sustained AF". Thus, as described herein, various exemplary methods and/or devices optionally stimulate parasympathetic nerves to decrease dispersion of refractoriness. Further, various exemplary methods and/or devices optionally stimulate parasympathetic nerves to increase conduction homogeneity. In general, such exemplary methods and/or devices optionally cause a vagal surge, which can remodel (e.g., typically temporarily) at least parts of the myocardial landscape and terminate SVAs. Remodeling may disrupt and/or stop reentrant wavefronts and thus terminate an SVA.

Parasympathetic Stimulation to Mimic Phase IV of Valsalva's Maneuver

As already mentioned, Valsalva's maneuver and/or other physical manipulation techniques may terminate SVAs. For example, a study by Wen et al., "Electrophysiological mechanisms and determinants of vagal maneuvers for termination of paroxysmal supraventricular tachycardia", *Circulation*, 98:2716–2723 (1998), reported that "of 85 patients with atrioventricular reciprocating tachycardia (AVRT), vagal maneuvers terminated in 45 (53%)" and "of 48 patients with atriventricular nodal reentrant tachycardia (AVNRT), vagal maneuvers terminated the tachycardia in the antegrade slow pathway (14%) or in the retrograde fast pathway (19%)". Wen et al., concluded that "both the vagal response and conduction properties of the reentrant circuit determine the tachycardia termination by vagal maneuvers". Valsalva's maneuver is often defined in four response phases: 1) an increase in arterial pressure and a decrease in heart rate upon straining; 2) a fall, then recovery of arterial pressure accompanied by an increase in heart rate; 3) a brief reduction of arterial pressure and increase in heart rate at the release of straining; and 4) a sustained elevation of arterial pressure and slowing of heart rate.

A mix of sympathetic and parasympathetic activity occurs during various phases. For example, sympathetic activity increases with withdrawal of the vagal response during phases 2 and 3, which can enhance antegrade AV node conduction velocity. Phase 4 involves vagal baroreflex responsiveness, which can be assessed by determining the change in R—R interval. The study by Wen et al., further noted that "in the AVRT group, the patients without termination of tachycardia by vagal maneuvers had similar BRS [baroreflex response] as those with termination, but their VM-induced baroreflex was much poorer". In particular, "for patients whose tachycardias were terminated antegradely by VM, tachycardias were interrupted mostly in phase IV". In addition, "because the antegrade AV node conduction was poorer and the Valsalva-baroreflex was better in these patients, tachycardia was more easily terminated by increase of vagal tone". Thus, various exemplary methods and/or devices optionally stimulate parasympathetic nerves to terminate SVA amendable to termination by Valsalva's maneuver.

Figure 3:
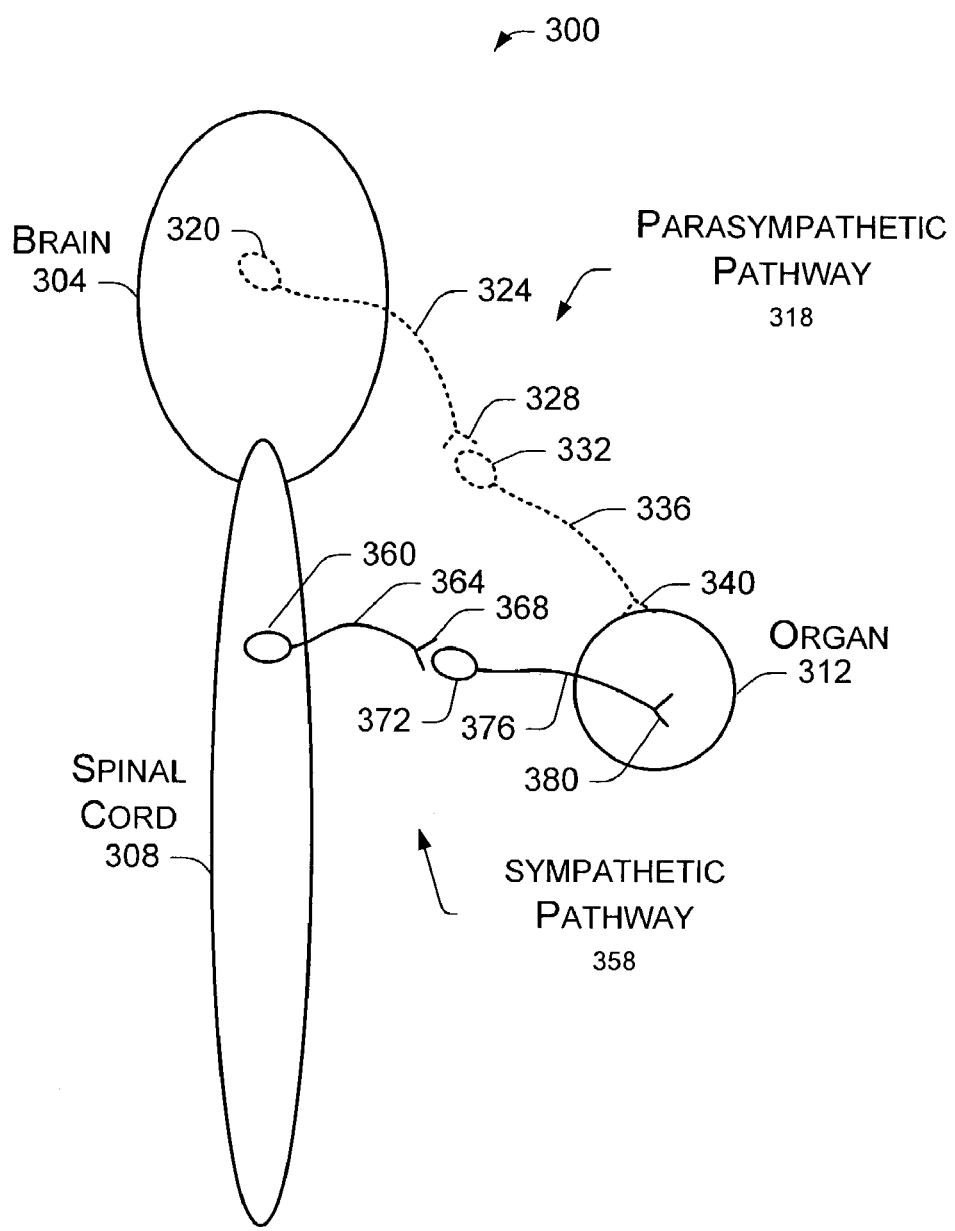
FIG. 3 is a simplified approximate anatomical diagram of a parasympathetic pathway and a sympathetic pathway of the autonomic nervous system.

As already mentioned, the autonomic nervous system includes parasympathetic and sympathetic pathways. Referring to FIG. 3, a simplified diagram of the autonomic nervous system 300 is shown. The system 300 illustrated includes a brain 304, a spinal cord 308, an organ 312, a parasympathetic efferent pathway 318 and a sympathetic efferent pathway 358. The parasympathetic efferent pathway 318 includes a preganglionic cell body 320 located in the brain 304, a preganglionic axon 324, a synaptic cleft 328, a postganglionic cell body 332, a postganglionic axon 336, and a postganglionic synaptic cleft 340 proximate to the organ 312. An exemplary parasympathetic stimulus originates at the brain 304 and ends at the postganglionic synaptic cleft 340 wherein a chemical is emitted to effect cell of the organ 312. A synaptic cleft may also be referred to as a neuroeffector junction. The sympathetic efferent pathway 358 includes a preganglionic cell body 360 located in the spinal cord 308, a preganglionic axon 364, a synaptic cleft 368, a postganglionic cell body 372, a postganglionic axon 376, and a postganglionic synaptic cleft 380 proximate to the organ 312. An exemplary sympathetic stimulus originates at the spinal cord 308 and ends at the postganglionic synaptic cleft 380 wherein a chemical is emitted to effect cell of the organ 312. In both pathways 318, 358, acetylcholine operates as a neurotransmitter to activate postganglionic neurons, i.e., preganglionic neurons are cholinergic. In parasympathetic pathways (e.g., the parasympathetic pathway 318), postganglionic neurons emit acetylcholine and are therefore cholinergic. However, in many sympathetic pathways (e.g., the sympathetic pathway 358), postganglionic neurons emit norepinephrine and are therefore adrenergic. While FIG. 3 shows a one to one ratio of preganglionic to postganglionic neurons, note that a preganglionic neuron generally links to more than one postganglionic neuron, for example, in a sympathetic pathway, a preganglionic neuron to postganglionic neuron ratio may be approximately 1:32. Autonomic pathways than can affect cardiac operation are described in more detail below.

Autonomic Pathways

As already mentioned, the autonomic nervous system includes both sympathetic and parasympathetic nerves. In general, the sympathetic nerves and parasympathetic nerves follow pathways, which, as described in more detail below, are at times to some degree intermingled. Intermingling in the vagosympathetic trunks includes, for example, fibers having a sympathetic core surrounded by a parasympathetic vagal skin. Such "vagosympathetic" fibers may arise from one of the vagosympathetic trunks and descend into epicardial and/or endocardial fibers of the heart. Parasympathetic pathways effecting cardiac operation include the vagus nerve, which is a member of a group of nerves commonly referred to as the cranial nerves. Scientifically, the vagus nerve has been designated as the tenth cranial nerve. There are two of these mixed nerves that act to provide both motor and sensory functions. Each vagus nerve contains both somatic and autonomic branches; however, the autonomic function predominates. Vagus nerves are parasympathetic in nature making up 75% of all parasympathetic fibers passing to the thoracic and abdominal regions of the body. As is the case with most nerves, vagi nerves contain both efferent fibers (e.g., to carry an impulse from its origin in the medulla obligata of the brain to a tissue or an organ), as well as afferent fibers, (e.g., to carry an impulse from a tissue or an organ back to the brain). With vagus nerves, 80% of the fibers are afferent as opposed to efferent. This aids in their active response to the many reflex actions in the body during parasympathetic control. As a whole, the two vagus nerves are very large and work to stimulate a great number of tissues in the body. Vagal stimulation can affect the heart, lungs, esophagus, stomach, small intestine, liver, gall bladder, as well as the upper portions of the ureters.

In general, the right and left vagus nerve pass down the neck as part of right and left vagosympathetic trunks. The right and left vagus also have branches that innervate the heart and lungs.

Regarding the heart, parasympathetic vagi nerves are distributed to regions of the SA node and the AV node. Release of acetylcholine to these regions typically results in both a decrease in the rate of rhythm of the SA node, as well as a decrease in the cardiac impulse transmission into the ventricles. Consequences of these actions generally include a decrease in heart rate, cardiac output, ventricular contraction, arterial blood pressure, as well as a decrease in overall ventricular pumping.

In general, the right vagus innervates the SA nodal region, the atrial muscle and, to a much lesser degree, the AV nodal region; whereas, the left vagus nerve innervates the SA nodal region and atrial muscle to a lesser degree than it innervates the AV nodal region. Stimulation of the right vagus nerve can predominately slow the SA node rate and thereby reduces heart rate; whereas, stimulation of the left vagus nerve can produce some slowing of the SA node, prolongation of AV conduction and partial or total AV block.

The vagi nerves are also involved in a process known as respiratory sinus arrhythmia (RSA). As stated in Mendelowitz, "Advances in parasympathetic control of heart rate and cardiac function", *News Physiol. Sci.*, 14:155–161 (1999), in RSA, "the heart beats more rapidly in inspiration and slows during postinspiration and expiration". Further, Mendelowitz noted that "cardiac vagal neurons recorded in vivo receive inhibitory synaptic input during inspiration, which is then followed by a rapid depolarization caused by excitatory synaptic input during postinspiration".

Figure 4:
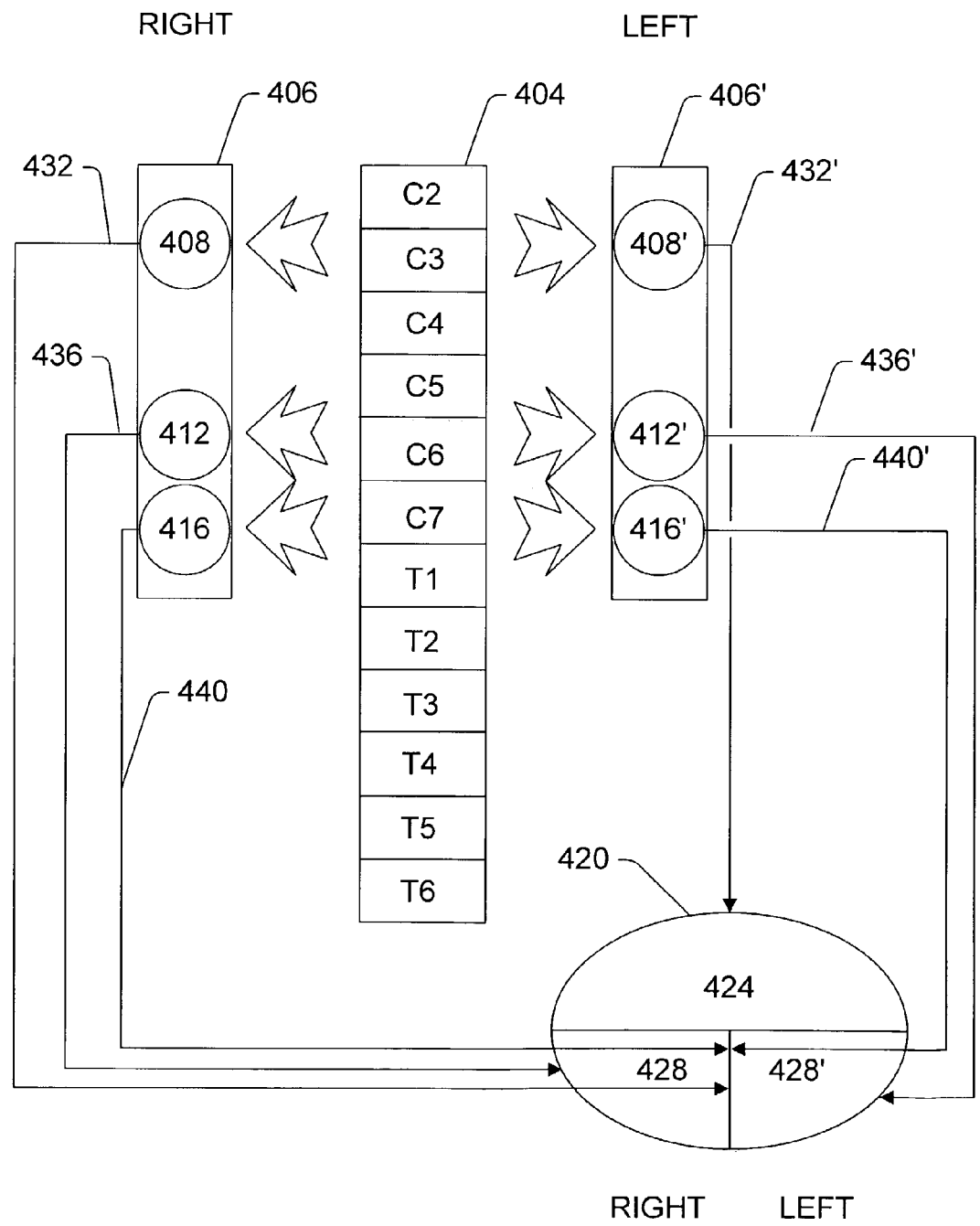
FIG. 4 is a simplified approximate anatomical diagram of sympathetic pathways and/or parasympathetic pathways to the heart.

Referring to FIG. 4, a block diagram of various components of the autonomic nervous system is shown. While FIG. 4 pertains primarily to sympathetic pathways, as already mentioned, intermingling of sympathetic pathways and parasympathetic pathways typically occurs to some degree at various points. The sympathetic nervous system, which is not part of the central nervous system, includes two parallel chains or trunks, a right trunk 406 and a left trunk 406'. Each trunk includes a series of ganglia which lie just lateral to the spinal cord 404 on each side (left and right). In general, the uppermost region of each trunk (406, 406') has three cervical ganglia, which are continuous with the thoracic trunk. The cervical ganglia are known as the right and left superior cervical ganglia (408, 408'), the right and left middle cervical ganglia (412, 412') and the right and left inferior cervical ganglia (416, 416'), the latter of which are known as a stellate ganglion if they combine with a respective first thoracic ganglion. Stellate ganglia exist in approximately 70% to approximately 80% of the population.

Cardiac sympathetic fibers originate in intermediolateral columns of the upper five or six thoracic segments (see T1–T6 in FIG. 4) and lower one or two cervical segments (see C5 and C6 in FIG. 4) of the spinal cord 404. Sympathetic fibers enter the paravertebral chain and typically synapse in the cervical ganglia. Cardiac sympathetic ganglia are generally found close to the spinal column (paravertebral ganglia) and may stem from both thoracic and cervical preganglionic fibers. Postganglionic cardiac sympathetic nerves originate from the left and right ganglia and usually approach the base of the heart (e.g., as superior, middle, and inferior cardiac nerves) along the adventitial surface of the great vessels.

Each of the superior cardiac nerves 432, 432' arises by two or more branches from a respective superior cervical ganglion 408, 408', and occasionally receives a filament from the trunk between a first and/or a second cervical ganglia. The right superior cardiac nerve 432, at the root of the neck, passes either in front of or behind the subclavian artery, and along the innominate artery to the back of the arch of the aorta, where it joins the deep part 428, 428' of the epicardial plexus 420. The right superior cardiac nerve 432 connects with other sympathetic branches. About the middle of the neck the right superior cardiac nerve 432 receives filaments from the external laryngeal nerve; lower down, one or two twigs from the vagus; and as it enters the thorax it is joined by a filament from the recurrent nerve. In addition, filaments from the nerve communicate with the thyroid branches from the right middle cervical ganglion 412. The left superior cardiac nerve 432', in the thorax, runs in front of the left common carotid artery and across the left side of the arch of the aorta, to the superficial part 424 of the epicardial plexus 420.

Each of the middle cardiac nerves 436, 436' (or great cardiac nerves), the largest of the three cardiac nerves, arises from a respective middle cervical ganglion 412, 412', or from a respective trunk 406, 406' between the middle ganglion 412, 412' and the inferior ganglion 416, 416'. On the right side, the right middle cardiac nerve 436 descends behind the common carotid artery, and at the root of the neck runs either in front of or behind the subclavian artery; it then descends on the trachea, receives a few filaments from the recurrent nerve, and joins the right half of the deep part 428 of the epicardial plexus 420. In the neck, it communicates with the right superior cardiac nerve 432 and recurrent nerve. On the left side, the left middle cardiac nerve 436' enters the chest between the left carotid and subclavian arteries, and joins the left half of the deep part 428' of the epicardial plexus 420.

Each inferior cardiac nerve 440, 440' arises from the respective inferior cervical ganglion 416, 416' or the first thoracic ganglion (or stellate ganglion, e.g., 416, 416'). Both right and left inferior cardiac nerves 440, 440' descend behind the subclavian artery and along the front of the trachea, to join the deep part 428, 428' of the epicardial plexus 420. Each of the inferior cardiac nerves 440, 440' communicates freely behind the subclavian artery with the recurrent nerve and the respective middle cardiac nerve 436, 436'.

As already mentioned with reference to FIG. 4, at the base of the heart, the sympathetic fibers form an epicardial plexus 420 that distributes the fibers to the various regions of the heart. The epicardial plexus 420 has a superficial part 424 and a deep part (shown as a right deep part 428 and a left deep part 428' in FIG. 4), see, e.g., *Gray's anatomy: the anatomical basis of medicine and surgery*, 38th ed. (1995). The deep part 428, 428' lies upon the tracheal bifurcation (at the back of the aorta and in front of the tracheal bifurcation) and consists of cardiac branches from all cervical sympathetic ganglia of both right and left sides except the superior left 408', together with superior and inferior cervical and thoracic cardiac branches of the right vagus nerve (parasympathetic) and superior cervical and thoracic branches of the left vagus nerve (parasympathetic).

Figure 5:
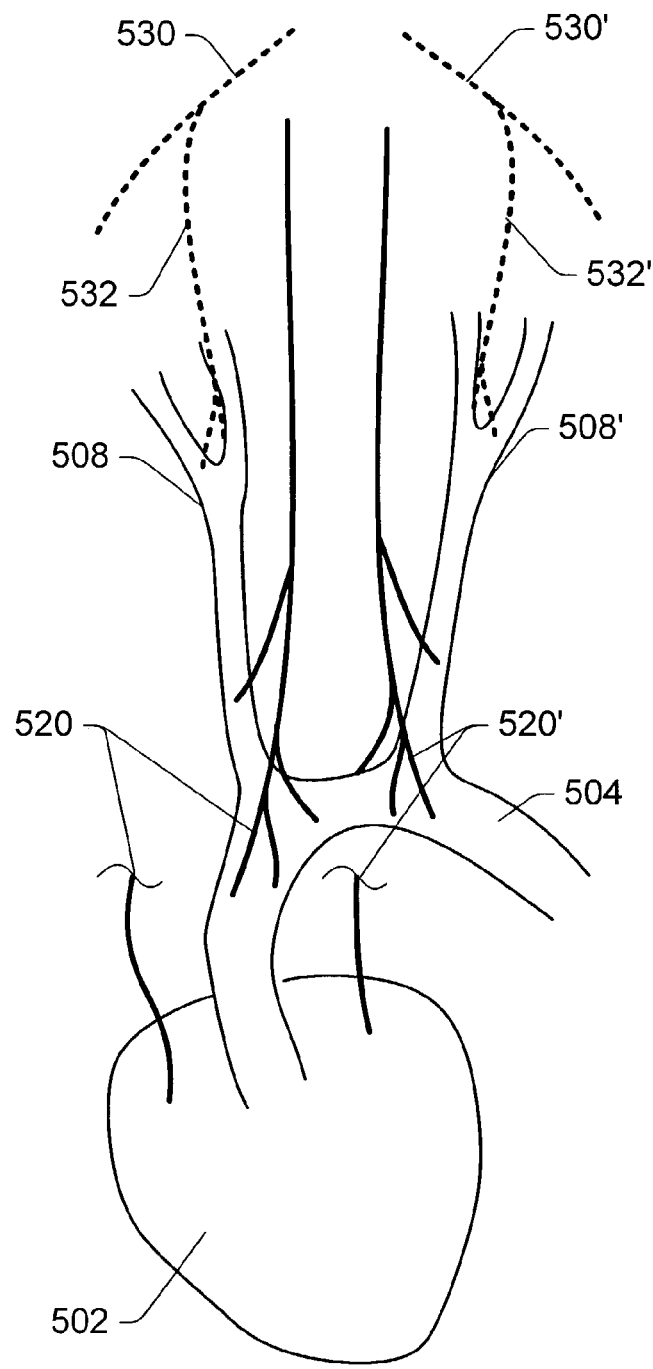
FIG. 5 is a simplified approximate anatomical diagram of parasympathetic afferent pathways.

Referring to FIG. 5, an approximate anatomical diagram of afferent vagal parasympathetic pathways 520, 520' is shown. Vagal afferent pathways include baroreceptors and/or chemoreceptors from the aortic arch 504, carotid arteries 508, 508' and the heart 502. With respect to the heart 502, vagus afferent pathways are known to have receptors associated with atria, ventricles, pulmonary arteries and coronary arteries. Also shown in FIG. 5 are the glossopharyngeal nerves 530, 530' and sinus branches thereof 532, 532'. In general, such afferent pathways lead to the nucleus tractus solitarius in the brainstem. In addition, stimulation of such afferent pathways typically leads to a depressor response. However, a controversial and seemingly undocumented (in humans) reflex known as the "Bainbridge reflex" can increase heart rate due to an increase of the right atrial pressure (e.g., tachycardia with hypervolemia). In general, cardiac receptors that lead to a neural response are classified as "A" or "B" receptors. B receptors are the predominant stretch receptors and are stimulated by passive stretch of the atria usually during later diastole. B receptors, when stimulated, cause a response similar to baroreceptors, e.g., inhibition of sympathetic nerves and/or excitation of parasympathetic nerves.

Another group of receptors known as left atrial volume receptors respond to increases in transmural pressure: e.g. from increased left atrial volume. Impulses transmitted to the osmoregulatory centers of the hypothalamus result in reduced ADH (antidiuretic hormone, vasopressin) secretion thereby increasing body water loss. Reflex hypotension and bradycardia sometimes follow left atrial distention. With hemorrhage and decreases in left atrial pressure, ADH secretion is increased to induce water retention. Receptors can also cause hormone secretion. For example, mammalian atria have secretory granules containing a small peptide, atrial natriuretic peptide (ANP). ANP is secreted on stretch of the atria. This potent, short lived peptide induces renal secretion of sodium and increase diuresis thus serving to decrease volume. ANP appears to act to decrease CO by decreasing systemic resistance and by increase capillary filtration.

Ventricular, mostly left ventricle, responses include the Bezold-Jarish Reflex, which results from ventricular wall distention stimulating ventricular mechanoreceptors. Such receptors appear to be active only with extreme conditions to protect the ventricle from volume overload (elicit hypotension and bradycardia). The response is a reflex vagal slowing of the heart and simultaneous inhibition of sympathoadrenal activity. The reflex protects against cardiac overstrain, pulmonary edema, and hypovolemia whenever cardiac distention is excessive (e.g., in some CHF patients). The reflex, transmitted by afferent vagal fibers, is thought to exert its sympathetic block via release of endogenous opiods likely acting on the delta-type opiod receptors in the brain.

Epicardial Autonomic Pathways

Pauza et al., "Morphology, distribution, and variability of the epicardiac neural ganglionated subplexuses in the human heart", *The Anatomical Record* 259(4): 353–382 (2000), reported that the epicardial plexus forms seven subplexuses: (I) left coronary, (II) right coronary, (III) ventral right atrial, (IV) ventral left atrial, (V) left dorsal, (VI) middle dorsal, and (VII) dorsal right atrial. Pauza et al., state that, in general, the human right atrium is innervated by two subplexuses (III, VII), the left atrium by three subplexuses (IV, V, VI), the right ventricle by one subplexus (II), and the left ventricle by three subplexuses (I, V, VI). Pauza et al., also note that diagrams from Mizeres, "The cardiac plexus in man", *Am. J. Anat.* 112:141–151 (1963), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava". Further, Pauza et al., also state that the left coronary (I), right coronary (II), ventral left atrial (IV) and middle dorsal (VI) subplexuses "may be considered as being formed by the deep extrinsic plexus that receives equally from both vagi and sympathetic trunks". Note that in the Pauza et al., reference, the terms "epicardiac preganglionated nerves" and "epicardiac postganglionated nerves" are differentiated from the meanings of "axons of the preganglionic and postganglionic neurons" that are valid in the nomenclature of the autonomic nervous system, for example, as referred to above with reference to FIG. 3 and FIG. 4. Thus, the term "postganglionic neurons" includes epicardiac/epicardial preganglionic neurons as well as epicardiac/epicardial postganglionic neurons.

Neuroeffectors

Upon stimulation, end terminals (or terminal knobs) of the postganglionic sympathetic nerves (e.g., epicardial postganglionic sympathetic nerves) release norepinephrine, which acts upon the myocardium. Following stimulation and release, norepinephrine remains active for several seconds; norepinephrine may then be reabsorbed by the terminal, diffuse out of the area, or be inactivated by enzymes. The adrenal medulla also secretes norepinephrine (e.g., 75 percent epinephrine and 25 percent norepinephrine) and produces a peripheral effect that typically lasts much longer than that produced by stimulation of the sympathetic postganglionic terminal knobs. While circulating norepinephrine can increase contractility, the effect on normally innervated hearts is relatively minor with respect to norepinephrine released by end terminals. Heart rate, although initially stimulated by norepinephrine, usually decreases over time due to activation of baroreceptors and vagal-mediated (parasympathetic) slowing of the heart rate.

Cardiac tissue membrane receptors, such as alpha receptors and beta receptors, receive chemicals emitted by postganglionic nerves. Alpha receptors are the most common type of sympathetic receptor and they respond strongly to norepinephrine and weakly to epinephrine. Beta receptors are also adrenergic and include beta-1, beta-2 and beta-3 receptors. Cardiac sympathetic receptors are mostly the beta-1 subtype. Beta-1 receptors, which respond approximately equally to norepinephrine and epinephrine, generally act on the myocardium to increase heart rate, contractility, and/or conduction velocity. In contrast, parasympathetic cholinergic muscarinic receptors act on the sinoatrial (SA) node to decrease heart rate and act on the atrioventricular (AV) node to decrease conduction velocity. Adrenergic antagonists (indirect action) include beta-blockers such as proranolol and alpha-blockers such as phentolamine that inhibit receptors. Cholinergic antagonists (indirect action) include alpha-blockers such as atropine.

Electrical and/or Magnetic Stimulation of Autonomic Nerves

Nerve stimulation may occur via electrical, magnetic and/or physical stimulation. Electrical stimulation of autonomic nerves has been reported in the literature, see, e.g., Murakami et al., "Effects of cardiac sympathetic nerve stimulation on the left ventricular end-systolic pressure-volume relationship and plasma norepinephrine dynamics in dogs", Jpn. Circ. J. 61(10): 864–71 (1997); and Du et al., "Response to cardiac sympathetic activation in transgenic mice overexpressing beta 2-adrenergic receptor". Am-J-Physiol. August; 271(2 Pt 2): H630–6 (1996). Magnetic stimulation of nerves has also been reported, for example, where a nerve is exposed to a time-varying magnetic field, which may induce electrical currents in the nerve.

According to various exemplary methods and/or devices described herein, a series of pulses, or a pulse train, is typically delivered by an implantable stimulation device to stimulate an autonomic nerve. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency include frequencies ranging from approximately 0.1 to approximately 100 Hz, and, in particular, frequencies ranging from approximately 1 Hz to approximately 20 Hz. Of course, higher frequencies higher than 100 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.05 milliseconds to approximately 2 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 4 V to approximately 15 V.

Vessels and Stimulation of Autonomic Pathways

According to various exemplary methods and stimulation devices described herein, and equivalents thereof, stimulation of parasympathetic nerves allows for influence of cardiac activity. For example, various exemplary methods and corresponding stimulation devices rely on placement of one or more electrodes in a vessel, e.g., an epicardial vein or other venous structure. Suitable epicardial veins or venous structures include the coronary sinus and veins that drain into the coronary sinus, either directly or indirectly. For example, the great cardiac vein passes along the interventricular sulcus, with the anterior interventricular coronary artery, and empties anteriorly into the coronary sinus; and the middle cardiac vein travels with the posterior (right) interventricular coronary artery and empties into the coronary sinus posteriorly. Other suitable veins include those that drain into the right atrium or right auricle. For example, the anterior cardiac vein passes through the wall of the right atrium and empties into the right atrium.

Other exemplary methods and/or devices rely on placement of one or more electrodes in a non-epicardial vein. Such exemplary methods and/or devices are optionally suitable for stimulation of parasympathetic nerves at locations, for example, generally along a parasympathetic pathway between the heart and brain. Further, other exemplary methods and/or devices rely on placing one or more electrodes through the wall of a vein and proximate to a parasympathetic nerve.

Figure 6:
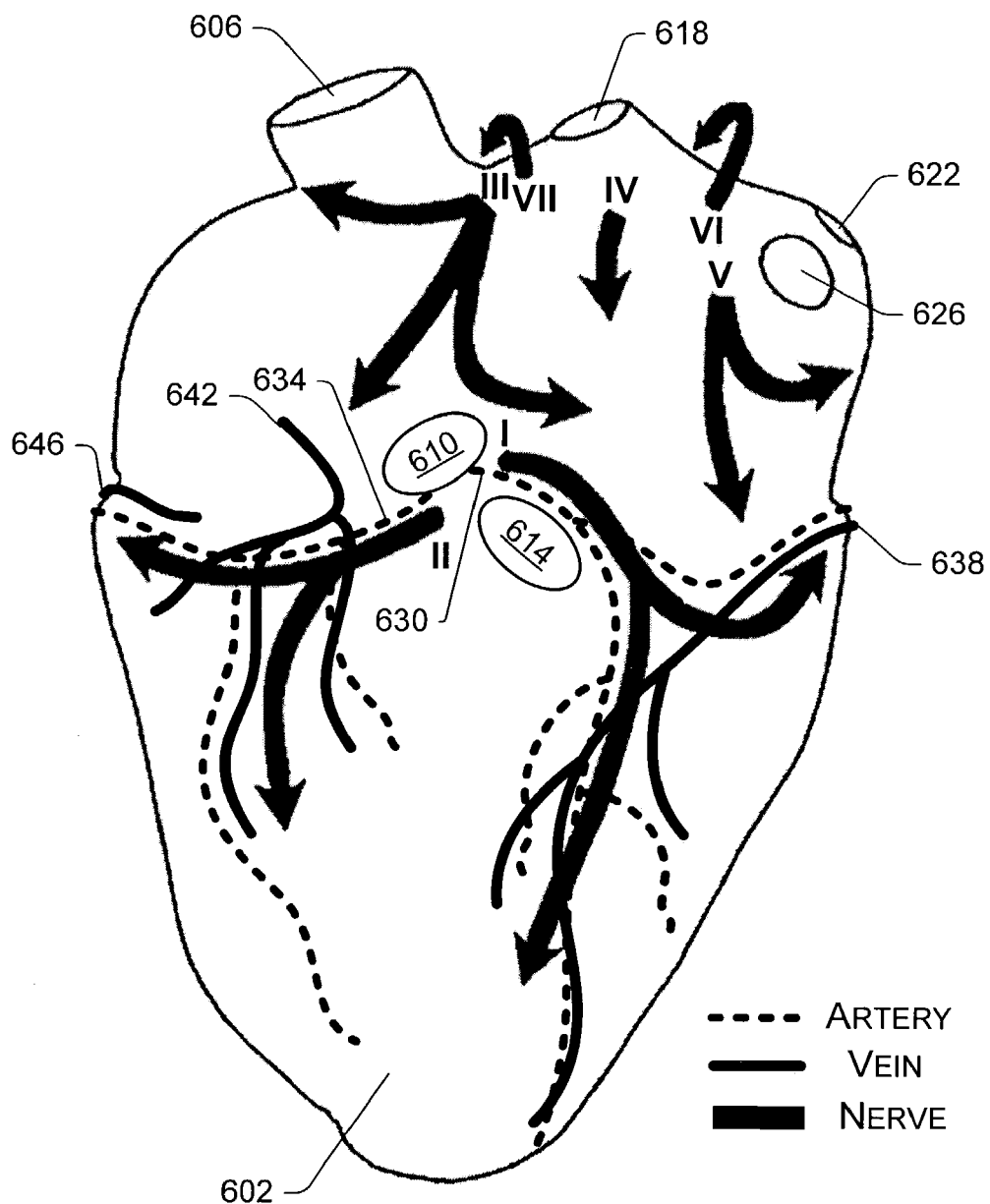
FIG. 6 is an approximate anatomical ventral view diagram of a human heart including some arteries, veins and nerves.

Referring to FIG. 6, a ventral diagram of a human heart 602 is shown. Various anatomical features of the heart 602 are also shown and include an opening to the superior vena cava 606, an opening to the aorta 610, an opening to the pulmonary trunk 614, an opening to the right superior pulmonary vein 618, an opening to the left inferior pulmonary vein 622, and an opening to the left superior pulmonary vein 626. FIG. 6 also shows some of the epicardial arteries (thick dashed lines) and veins (thick solid lines). Under normal conditions, epicardial arteries carry oxygenated blood to the myocardium, primarily myocardium of the ventricles while epicardial veins carry blood deoxygenated by the myocardium to the right atrium of heart 602. Pressure in the veins is much less than pressure in the arteries.

Two major epicardial arterial networks are shown in FIG. 6 and associated with the left coronary artery 630 and the right coronary artery 634. The left coronary artery 630 stems from the aorta near the opening to the aorta 610 and travels along the base of the left ventricle where it branches. One branch of the left coronary artery travels on the epicardial surface of the left ventricle toward the apex of the heart 602 (known as the left anterior descending artery) while another branch travels on the epicardial surface of the left ventricle toward the dorsal side of the heart 602 (known as the circumflex branch of the left coronary artery). The right coronary artery 634 stems from the aorta near the opening to the aorta 610 and travels along the base of the right ventricle where it branches. Various branches of the right coronary artery 634 travel on the epicardial surface of the right ventricle while at least one branch travels on the epicardial surface of the right ventricle toward the dorsal side of the heart 602.

Three major epicardial venous networks are shown in FIG. 6, which are associated with the great cardiac vein 638, the anterior cardiac vein 642, and the small cardiac vein 646. The great cardiac vein 638 receives blood from a network that spreads across the ventral side of the epicardial surface of the left ventricle and major branches of the network extend toward the apex of the heart 602. As already mentioned, the great cardiac vein 638 travels on the epicardial surface near the base of the left ventricle to the dorsal side of the heart 602 where it joins the coronary sinus vein. The anterior cardiac vein 642 receives blood from a network that spreads across the ventral and dorsal sides of the epicardial surface of the right ventricle and major branches of the network extend toward the apex of the heart 602. As already mentioned, the anterior cardiac vein empties into the right atrium of the heart 602. The small cardiac vein 646 travels from the ventral epicardial surface to the dorsal epicardial surface where it empties into the coronary sinus.

FIG. 6 also shows the seven subplexuses as identified by Pauza et al. Preganglionate nerves enter the left coronary subplexus (I) and the right coronary subplexus (II) approximately between the opening to the aorta 610 and the opening to the pulmonary trunk 614. Preganglionate nerves enter the ventral right atrial subplexus (III) at the superior interatrial sulcus and non-regularly on the ventral surface of the root of the superior vena cava while preganglionated nerves enter the ventral left atrial subplexus (IV) approximately between the superior interatrial sulcus and left atrial nerve fold. Preganglionated nerves enter the left dorsal subplexus (V) approximately at the left atrial nerve fold and preganglionated nerves enter the middle dorsal subplexus (VI) approximately between the right and left superior pulmonary veins (see, e.g., 618, 626) and, non-regularly, between the right pulmonary veins and the inferior vena cava. Preganglionated nerves enter the dorsal right atrial subplexus (VII) approximately between the superior vena cava and the right superior pulmonary vein (see, e.g., 606, 618). As already mentioned, postganglionated nerves, and some preganglionated nerves, spread out from the subplexuses (I–VII) across the epicardial surface of the heart 602. The spreading of such nerves is shown by the thick solid arrows in FIG. 6 and FIG. 6, the latter of which shows a dorsal diagram of the heart 602.

Figure 7:
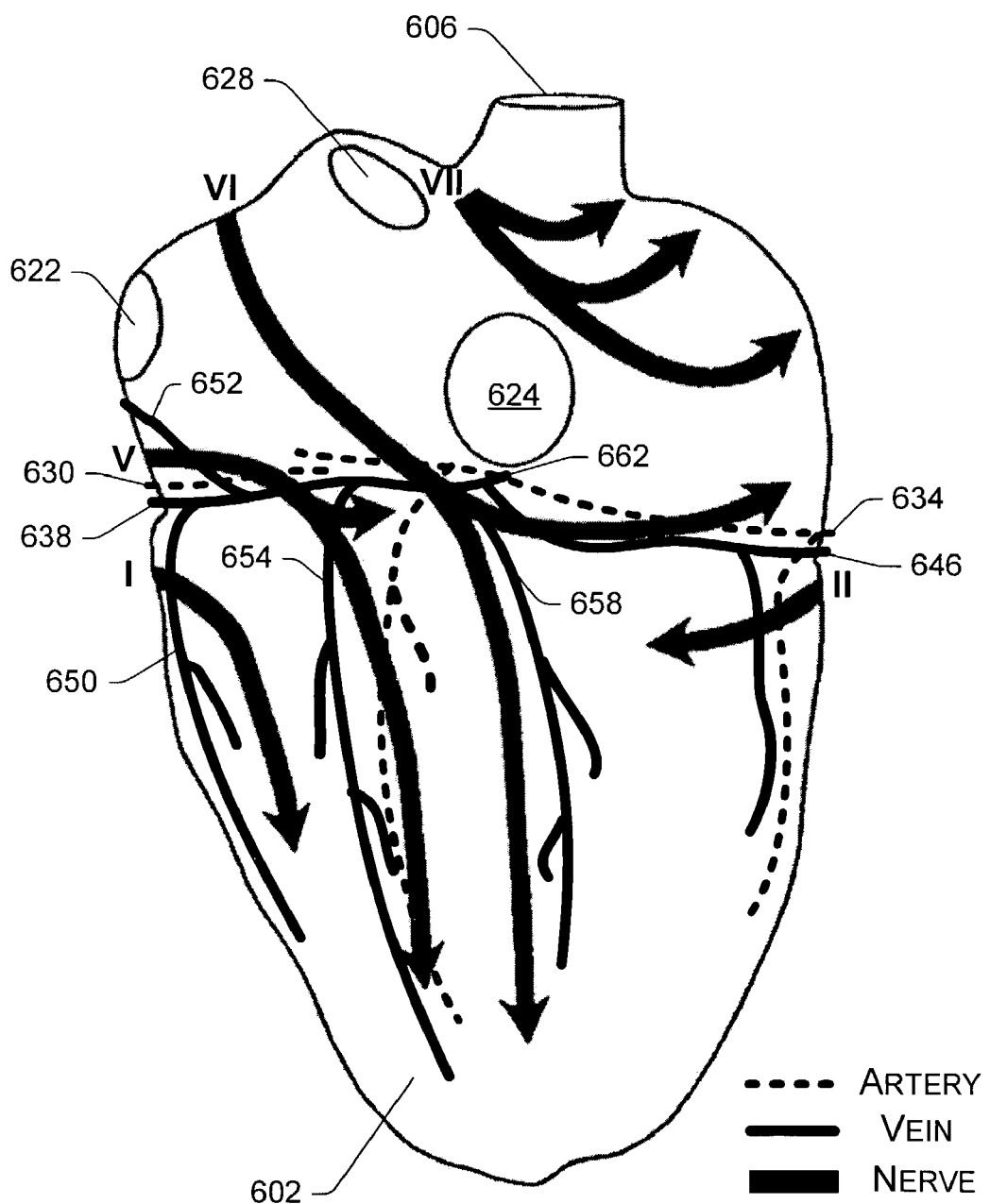
FIG. 7 is an approximate anatomical dorsal view diagram of a human heart including some arteries, veins and nerves.

Referring to FIG. 7, a dorsal diagram of the human heart 602 is shown. Various anatomical features of the heart 602 are also shown and include an opening to the superior vena cava 606, an opening to the inferior vena cava 624, an opening to the right inferior pulmonary vein 628, and an opening to the left inferior pulmonary vein 622. FIG. 7 also shows some of the epicardial arteries (thick dashed lines) and veins (thick solid lines). The arterial and venous networks shown on the dorsal epicardial surface of the heart 602 include extensions of networks from the ventral epicardial surface. For example, the dorsal epicardial surface includes networks stemming the right coronary artery 634 and the left coronary artery 630. In particular, the circumflex branch of the left coronary artery 630 is shown along with various extensions of the right coronary artery 634 one of which approaches the end of the circumflex branch. Venous epicardial structures shown in FIG. 6 include the coronary sinus 662, the great cardiac vein 638, the small cardiac vein 646, the oblique vein of the left atrium 652, the left marginal vein 650, the posterior vein of the left ventricle 654, and the middle cardiac vein 658. The aforementioned veins (638, 646, 650, 652, 654, 658) empty into the coronary sinus 662.

FIG. 7 also shows, via thick solid arrows, neural extensions of five of the subplexuses as identified by Pauza et al. Neural extensions of the left coronary subplexus (I) descend toward the apex of the heart 602 at and/or near the left marginal vein 650 and the posterior vein of the left ventricle 654. Neural extensions of the right coronary subplexus (II) traverse the heart 602 at and/or near the right coronary sulcus. Neural extensions of the left dorsal subplexus (V) descend toward the apex of the heart 602 at and/or near the posterior vein of the left ventricle 654 while neural extensions of the middle dorsal subplexus (VI) descend towards the apex of the heart 602 at and/or near the middle cardiac vein 658 and the small cardiac vein 646. Neural extensions of the dorsal right atrial subplexus (VII) extend around the right atrium at and/or near the superior vena cava (see, e.g., 606) and the inferior vena cava (see, e.g., 624).

As shown in FIGS. 6 and 7, various epicardial veins or venous structures travel at and/or near epicardial subplexuses and/or epicardial extensions of epicardial subplexuses. According to various exemplary methods and/or stimulation devices described herein, at least one electrode is placed in the lumen of an epicardial vein or venous structure and/or through the wall of an epicardial vein or venous structure. Further, upon passing current through the at least one electrode, neural stimulation occurs, which preferably causes release of a neuroeffector, such as, but not limited to, acetylcholine.

Stimulation of Parasympathetic Pathways

A study by Kawada et al., "Vagosympathetic interactions in ischemia-induced myocardial norepinephrine and acetylcholine release", Am. J. Physiol. Heart Circ. Physiol., 280: H216–H221 (2001), noted that "the present results imply that the antifibrillatory effect of electrical vagal stimulation is a direct effect of ACh [acetylcholine] on the myocardium rather than the presynaptic inhibition of NE release by ACh". Therefore, according to various exemplary methods described herein, an implantable device delivers one or more stimulation pulses to one or more electrodes located proximate to a parasympathetic pathway. Such an exemplary method may aim to stimulate a parasympathetic nerve (e.g., a vagal nerve) and cause release of acetylcholine to thereby produce an antifibrillatory and/or antiarrhythmic effect. As such, parasympathetic stimulation includes stimulation of afferent and/or efferent nerves. Of course, antifibrillatory and/or antiarrhythmic effects may result from other parasympathetic mechanisms induced by stimulation of a parasympathetic nerve.

Figure 8:
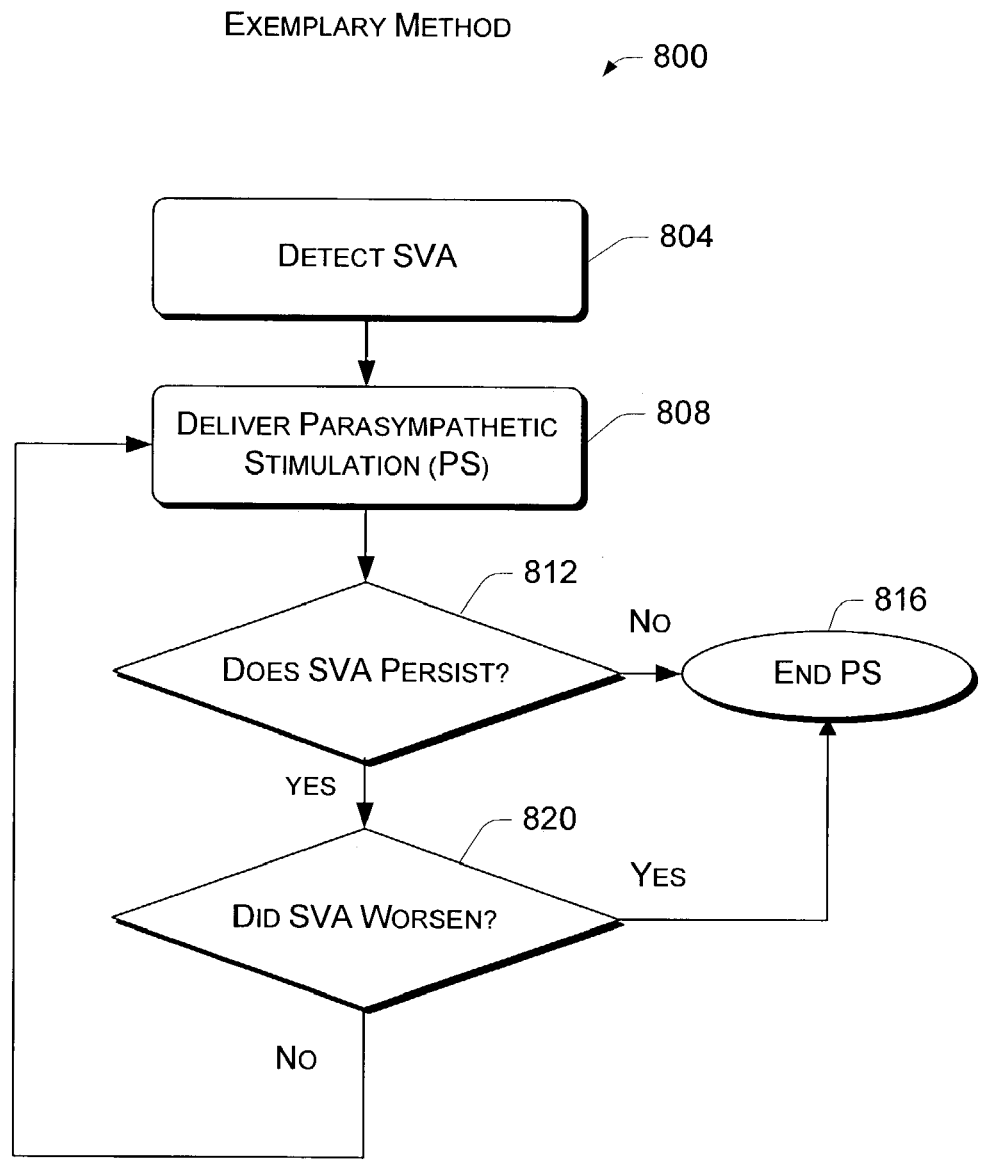
FIG. 8 is a block diagram of an exemplary method for stimulating a parasympathetic nerve in response to detection of a supraventricular arrhythmia (SVA).

Referring to FIG. 8, after an initial positioning of one or more electrodes proximate to a parasympathetic nerve, an exemplary method involves delivering a stimulation pulse to the one or more electrodes to thereby stimulate the parasympathetic nerve. More specifically, as shown in FIG. 8, in a detection block 804, a stimulation and/or other device detects a SVA. SVA detection may occur according to one or more detection techniques, some of which have been described herein. Next, in a delivery block 808, a stimulation device delivers a stimulation pulse (e.g., a single pulse, a series of pulses or pulse train, etc.) to one or more electrodes positioned proximate to a parasympathetic nerve in an effort to terminate the SVA. For example, the parasympathetic stimulation may act to lengthen an excitable gap of one or more reentrant circuits involved in the SVA. The exemplary method 800 optionally delivers a proscribed pacing therapy in conjunction with parasympathetic stimulation. In such an example, alteration of the proscribed pacing therapy, while optional, may not be required. However, if the parasympathetic stimulation acts to increase an excitable gap, then delivery of one or more pacing pulses, e.g., ventricular and/or atrial, may act to terminate the SVA. In practice, after lengthening of an excitable gap, a proscribed pacing pulse may have a greater probability of interrupting one or more reentrant circuits without further intervention.

A decision block 812 follows wherein a determination is made as to whether the SVA persists. If the SVA no longer persists, then the method 800 continues in an end block 816, which halts or ramps down parasympathetic stimulation (e.g., ramping down power as a function of time or a function of one or more cardiac events). However, if the SVA persists, then the method 800 continues in another decision block 820. The decision block 820 determines whether the SVA worsened or improved. In general, worsening is typically associated with an SVA becoming more complex whereas improving is typically associated with an SVA becoming less complex. Hence, the exemplary method 800 may make one or more determinations such as whether an SVA terminated, became more complex or became less complex. Of course, various other states may be defined and/or determined. In general, an exemplary method takes appropriate action based on the state of an SVA; however, other factors may be taken into account as well (e.g., AV conduction, phase of respiratory cycle, characteristics of a normal or abnormal cardiac cycle, etc.). For example, if parasympathetic stimulation according to a stimulation site and stimulation parameters is likely to cause a significant degree of AV block, then an appropriate course of action may include ventricular pacing, if available. Of course, an exemplary method may optionally determine whether some degree of AV block exists and take appropriate action in response thereto (e.g., halting parasympathetic stimulation, ventricular pacing, etc.).

With respect to determining whether characteristics of an SVA have changed (e.g., complexity, improvement, worsening, etc.), an implantable stimulation device may receive information from one or more sensors such as, motion sensors, position sensors, electrical activity sensors, pH sensors, gas sensors, etc., and use such information to determine one or more characteristics of the SVA. For example, an electrical activity sensor may allow a device to determine if amplitude of atrial activity has increased, which may indicate the presence of more coherent or homogeneous atrial activity, if an atrial rate has fallen below some threshold rate (e.g., 120 bpm, etc.), and/or whether atrial activity exhibits any periodicity. Of course, ventricular activity may aid in detecting an SVA, determining state of an SVA, and/or in the adjustment of one or more parasympathetic stimulation parameters.

Referring again to the exemplary method 800 of FIG. 8, if the decision block 820 determines that the SVA worsened, then the method 800 continues in the end block 816, wherein parasympathetic stimulation is typically halted immediately. However, if the decision block 820 determines that the SVA did not worsen (e.g., improved or condition unchanged), then the method 800 may continue in the delivery block 808. In this example, the parasympathetic stimulation may continue according to one or more prior stimulation parameters (e.g., power, duty, amplitude, frequency, phase, polarity, stimulation site, etc.) or an adjustment block may adjust one or more of the one or more parameters, for example, based on characteristics of the SVA and/or other factors. For example, an implantable stimulation device may receive information from one or more sensors, such as, motion sensors, position sensors, electrical activity sensors, pH sensors, gas sensors, etc., and use such information to determine or adjust one or more parasympathetic stimulation parameters.

As already mentioned, if in the decision block 812, if the SVA no longer persists, then the end block 816 may halt or ramp down parasympathetic stimulation. In general, ramping down may provide for a prophylactic effect that reduces risk of reoccurrence of the SVA. Ramping down may occur as a function of time and/or as a function of one or more cardiac events, such as, a number of R waves, etc.

The exemplary method 800 optionally includes atrial pacing, for example, antitachycardia pacing. For example, upon detection of an SVA, overdrive pacing may occur in conjunction with appropriate parasympathetic stimulation. The exemplary method 800 may optionally include a cycle limit for parasympathetic stimulation. For example, a decision block may determine whether a cycle limit has been reached wherein if a cycle limit has not been reached, then the method 800 continues by returning to the parasympathetic stimulation delivery block 808 for delivering parasympathetic nerve stimulation. Whereas, if the cycle limit has been reached, then, in a change therapy block may cause a stimulation device to change therapy.

According to such an exemplary method 800, a stimulation and/or other device optionally determines an approximate location of SVA origin. For example, a reentrant loop driving an SVA may occur wholly or partly in the left atrium, the right atrium, and/or another structure. As already mentioned, patients may have reoccurring SVA with origin of determinable geometry and location. Indeed, such determinations are often made prior to ablation therapy. However, rather than ablation, such exemplary methods optionally determine location and then direct parasympathetic stimulation to affect the determined location.

Figure 9:
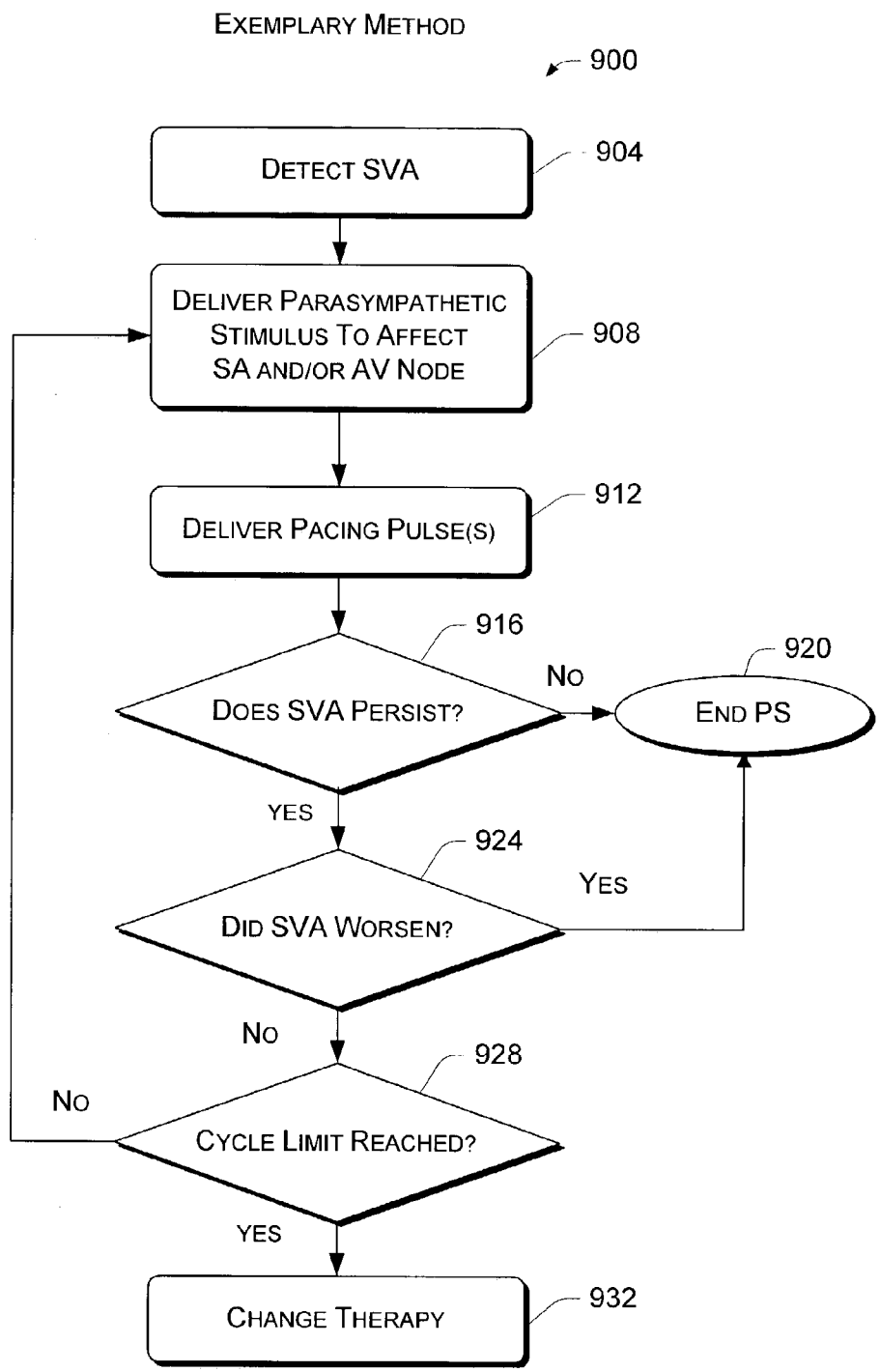
FIG. 9 is a block diagram of an exemplary method for stimulating a parasympathetic nerve to affect operation of a SA node and/or an AV node.

Referring to FIG. 9, after an initial positioning of one or more electrodes, via a vein, proximate to a parasympathetic nerve, an exemplary method involves delivering a stimulation pulse to the one or more electrodes to thereby stimulate the parasympathetic nerve. More specifically, as shown in FIG. 9, in a detection block 804, a stimulation and/or other device detects a SVA. Next, in a delivery block 808, a stimulation device delivers a stimulation pulse to one or more electrodes positioned proximate to a parasympathetic nerve to affect operation of the SA node and/or AV node. In this particular exemplary method 900, the stimulation device delivers a proscribed pacing therapy in conjunction with parasympathetic stimulation. In particular, alteration of the proscribed pacing therapy, while optional, is not required. Thus, following the delivery block 908, in another delivery block 912, the stimulation device delivers one or more pacing pulses, e.g., ventricular and/or atrial. In practice, after affecting the SA node and/or AV node, a proscribed pacing pulse may interrupt one or more SVAs without further intervention.

Following delivery of a parasympathetic pulse, or optionally a series of pulses, and a proscribed pacing pulse or pulses, in a determination block 916, the stimulation and/or other device determines whether the SVA persists. If the SVA does not persist, then the method 900 terminates in an end parasympathetic stimulation (PS) block 920. However, if the SVA persists, then in another determination block 924, the stimulation and/or other device determines whether the SVA worsened. Again, under certain conditions (e.g., autonomic imbalance, stimulants, etc.) parasympathetic stimulation may act to induce and/or prolong SVAs; therefore, this particular block ensures that the parasympathetic stimulation, as delivered in block 908, terminates to avoid worsening a patient's condition. As shown in FIG. 9, if the SVA worsens, then PS terminates in the end PS block 920. If the SVA does not worsen, then, in yet another determination block 928, the stimulation device determines whether a cycle limit has been reached, if applicable. If a cycle limit has not been reached, then the method 900 continues by returning to the parasympathetic stimulation delivery block 908 for delivering a stimulus to a parasympathetic nerve. If the cycle limit has been reached, then, in a change therapy block 932, the stimulation device changes the therapy.

According to such an exemplary method 900, a stimulation and/or other device optionally determines an approximate location of SVA origin. For example, a reentrant loop driving an SVA may occur wholly or partly in the left atrium, the right atrium, and/or another structure. Further, one or more SVAs may involve the SA node and/or the AV node. As already mentioned, patients may have reoccurring SVA with origin of determinable geometry and location. Indeed, such determinations are often made prior to ablation therapy. However, rather than ablation, such exemplary methods optionally determine location and then direct parasympathetic stimulation to affect the determined location.

Figure 10:
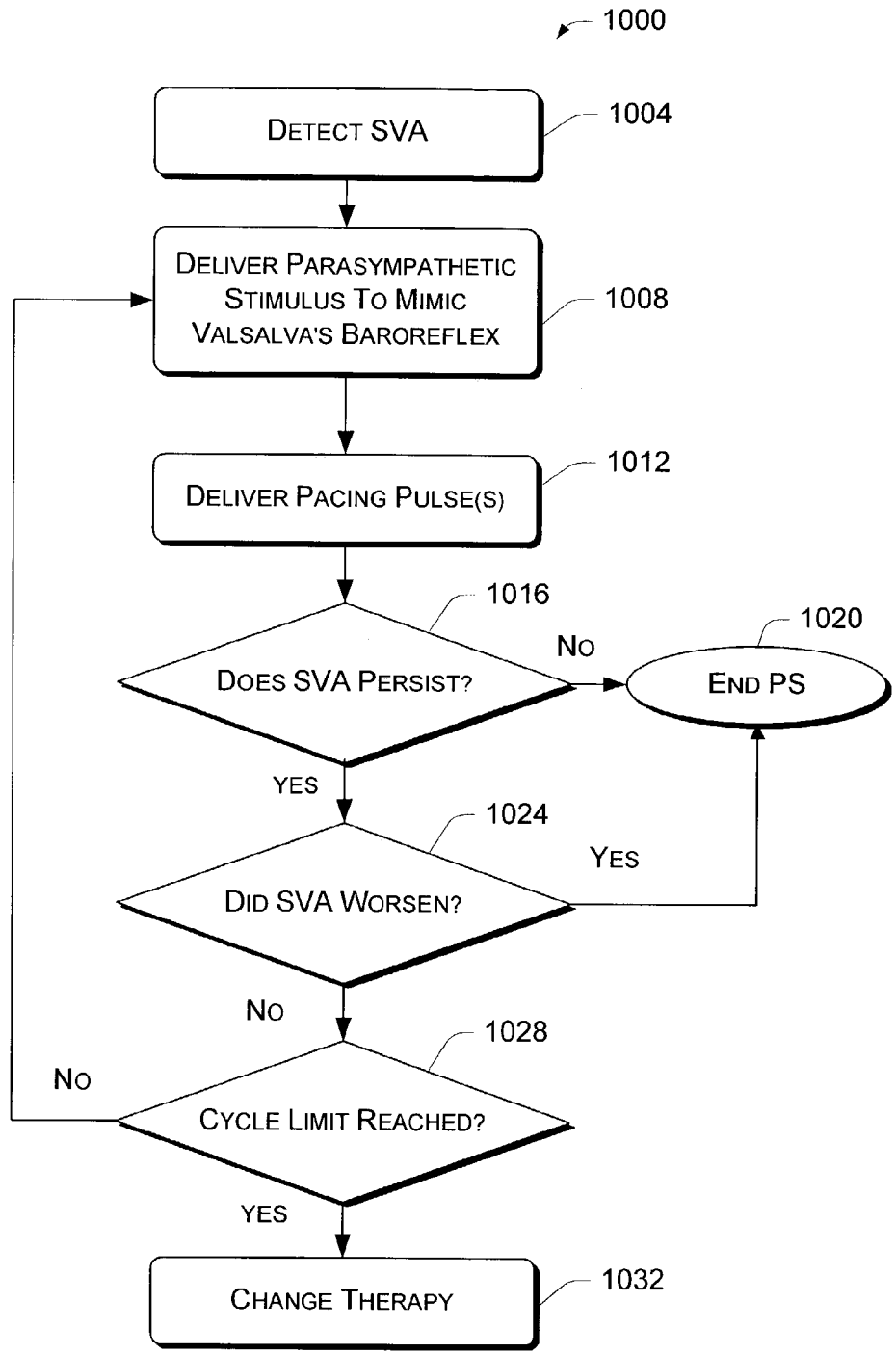
FIG. 10 is a block diagram of an exemplary method for stimulating a parasympathetic nerve to elicit a baroreflex response.

Referring to FIG. 10, after an initial positioning of one or more electrodes proximate to a parasympathetic nerve, an exemplary method involves delivering a stimulation pulse to the one or more electrodes to thereby stimulate the parasympathetic nerve. More specifically, as shown in FIG. 10, in a detection block 1004, a stimulation and/or other device detects a SVA. Next, in a delivery block 1008, a stimulation device delivers a stimulation pulse to one or more electrodes positioned proximate to a parasympathetic nerve (e.g., an afferent nerve of a parasympathetic pathway, etc.) to mimic the baroreflex response associated with Valsalva's maneuver. In this particular exemplary method 1000, the stimulation device delivers a proscribed pacing therapy in conjunction with parasympathetic stimulation. In particular, alteration of the proscribed pacing therapy, while optional, is not required. Thus, following the delivery block 1008, in another delivery block 1012, the stimulation device delivers one or more pacing pulses, e.g., ventricular and/or atrial. In practice, after initiating a baroreflex response via parasympathetic stimulation, a proscribed pacing pulse may interrupt one or more SVAs without further intervention.

Following delivery of a parasympathetic pulse, or optionally a series of pulses, and a proscribed pacing pulse or pulses, in a determination block 1016, the stimulation and/or other device determines whether the SVA persists. If the SVA does not persist, then the method 1000 terminates in an end parasympathetic stimulation (PS) block 1020. However, if the SVA persists, then in another determination block 1024, the stimulation and/or other device determines whether the SVA worsened. Again, under certain conditions (e.g., autonomic imbalance, stimulants, etc.) parasympathetic stimulation may act to induce and/or prolong SVAs; therefore, this particular block ensures that the parasympathetic stimulation, as delivered in block 1008, terminates to avoid worsening a patient's condition. As shown in FIG. 10, if the SVA worsens, then PS terminates in the end PS block 1020. If the SVA does not worsen, then, in yet another determination block 1028, the stimulation device determines whether a cycle limit has been reached, if applicable. If a cycle limit has not been reached, then the method 1000 continues by returning to the parasympathetic stimulation delivery block 1008 for delivering a stimulus to a parasympathetic nerve. If the cycle limit has been reached, then, in a change therapy block 1032, the stimulation device changes the therapy.

According to such an exemplary method 1000, a stimulation and/or other device optionally determines an approximate location of SVA origin. For example, a SVA may occur wholly or partly in the left atrium, the right atrium, and/or another structure. As already mentioned, patients may have reoccurring SVA with determinable geometry and location. Indeed, such determinations are often made prior to ablation therapy. However, rather than ablation, such exemplary methods optionally determine location and then direct parasympathetic stimulation to affect the determined location in addition to eliciting a baroreflex response.

While the foregoing exemplary methods 800, 900, 1000 have been set forth as separate methods, combination of the various blocks within these methods is also possible. In addition, according to various exemplary methods (e.g., 800, 900, 1000) and/or devices, parasympathetic stimulation occurs optionally at a non-epicardial location and/or at an epicardial location. For example, suitable non-epicardial locations include, but are not limited to, right and left cervical vagal locations. Of course, locations also optionally include those associated with afferent parasympathetic pathways.

Stimulation of Epicardial Parasympathetic Pathways

Figure 11:
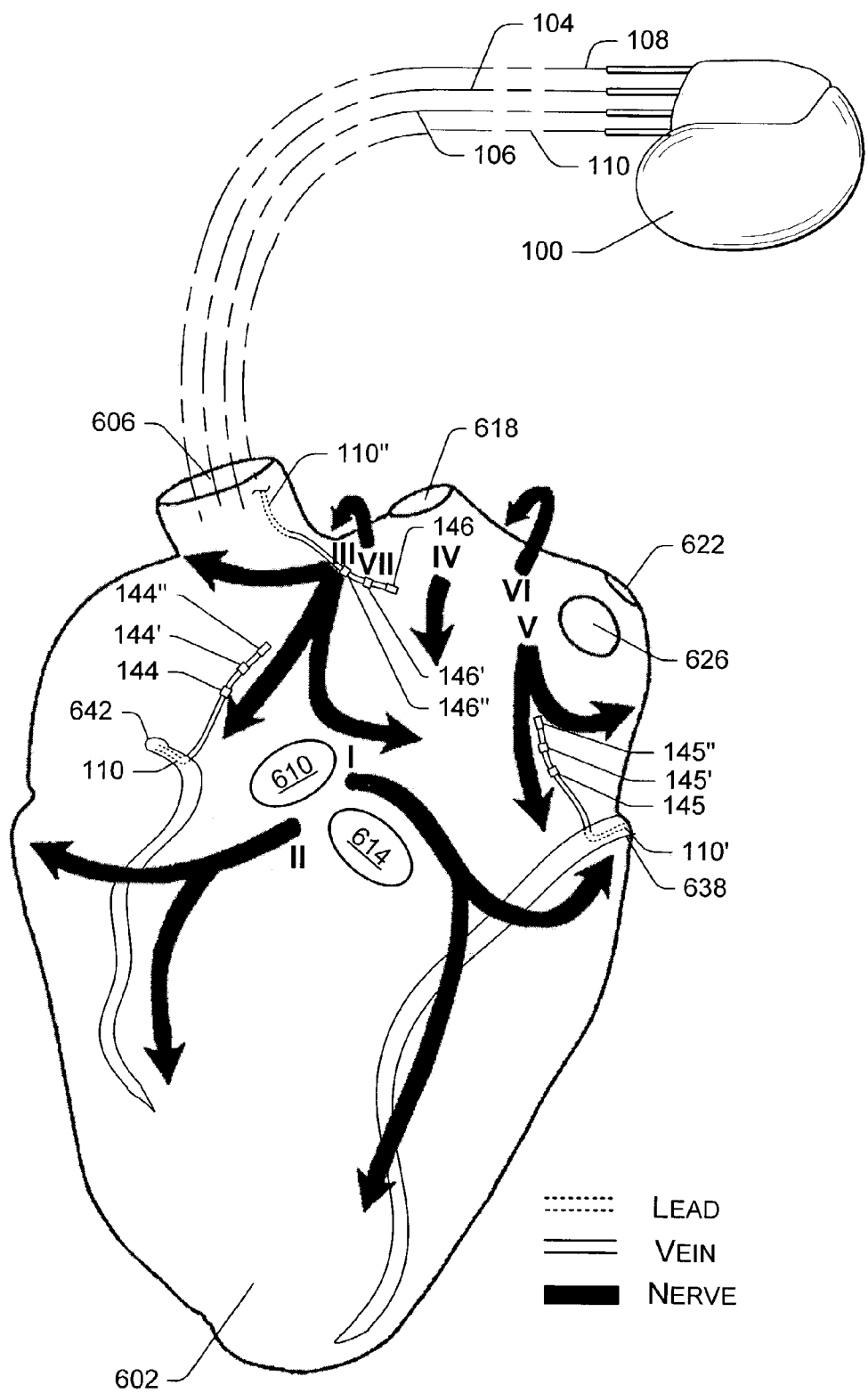
FIG. 11 is an approximate anatomical ventral view diagram of a human heart including some arteries, veins and nerves and stimulation leads associated with a pacing device.

Referring again to FIGS. 6 and 7, various epicardial vessels are shown along with various subplexuses. Referring to FIG. 11, an approximate anatomical diagram of a ventral view of a heart that corresponds to the diagram of FIG. 6 is shown. In FIG. 11, exemplary leads having exemplary electrodes are also shown in exemplary epicardial locations. For example, FIG. 11 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 11, one exemplary lead 110 has an electrode portion having three electrodes 144, 144', 144". The electrode portion of the lead 110 passes through the wall of the anterior cardiac vein 642 and extends along nerves emanating from the VRA (III) subplexus. Having an electrode portion of a lead positioned as such, activation of at least one of the electrodes 144, 144', 144" optionally stimulate nerves to release acetylcholine and/or affect operation of the SA node. In a similar manner, another exemplary lead 110' has an electrode portion having three electrodes 145, 145', 145". The electrode portion of the lead 110' passes through the wall of the great cardiac vein 638 and extends along nerves emanating from the LD (V) subplexus. Having an electrode portion of a lead positioned as such, activation of at least one of the electrodes 145, 145', 145" optionally stimulate nerves to release acetylcholine and/or affect operation of the AV node. Yet another exemplary lead 110" has an electrode portion having three electrodes 146, 146', 146". The electrode portion of the lead 110" passes through the wall of the superior vena cava (see, e.g., opening of superior vena cava labeled 606) and extends to the VRA (III) subplexus and/or DRA (VII) subplexus. Having an electrode portion of a lead positioned as such, activation of at least one of the electrodes 146, 146', 146" optionally stimulate nerves to release acetylcholine and/or affect operation of the SA node. Of course, the locations and functions of the three leads 110, 110', 110" are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference. While the leads shown in FIG. 11 include electrode portions that extend through a vessel and/or chamber wall, other exemplary leads include electrode portions that remain within the lumen of a vessel and/or within a chamber of the heart. Again, such leads optionally extend to pre-ganglionated field regions, ganglionated field regions and/or post-ganglionated field regions associated with at least one of the seven subplexus identified in the Pauza et al. reference. Further, exemplary leads optionally include electrode portions that remain within the lumen of a vessel and/or within a chamber of the heart.

Figure 12:
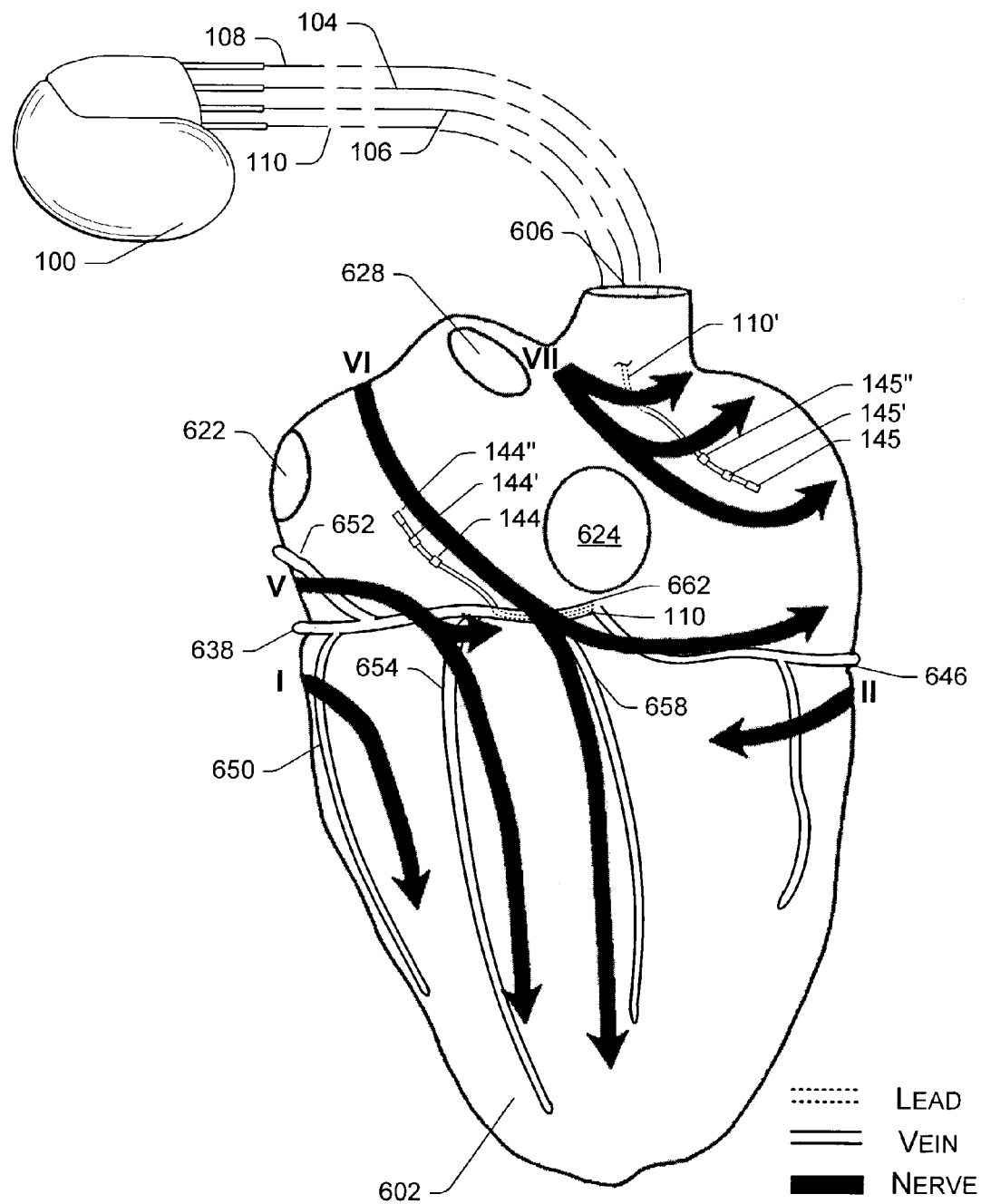
FIG. 12 is an approximate anatomical dorsal view diagram of a human heart including some arteries, veins and nerves and stimulation leads associated with a pacing device.

Referring to FIG. 12, an approximate anatomical diagram of a ventral view of a heart that corresponds to the diagram of FIG. 7 is shown. FIG. 12 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 12, one exemplary lead 110 has an electrode portion having three electrodes 144, 144', 144". The electrode portion of the lead 110 passes through the wall of the coronary sinus 662 and extends along nerves emanating from the MD (VI) subplexus and/or LD (V) subplexus. Having an electrode portion of a lead positioned as such, activation of at least one of the electrodes 144, 144', 144" may stimulate nerves to release acetylcholine and/or affect operation of the AV node. In a similar manner, another exemplary lead 110' has an electrode portion having three electrodes 145, 145', 145". The electrode portion of the lead 110' passes through the wall of the superior vena cava (see, e.g., opening of superior vena cava labeled 606) and extends to the DRA (VII) subplexus and/or to nerves emanating from the DRA (VII) subplexus. Having an electrode portion of a lead positioned as such, activation of at least one of the electrodes 145, 145', 145" may stimulate nerves to release acetylcholine and/or affect operation of the SA node. Of course, the locations and functions of the two leads 110, 110' are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference.

Figure 13:
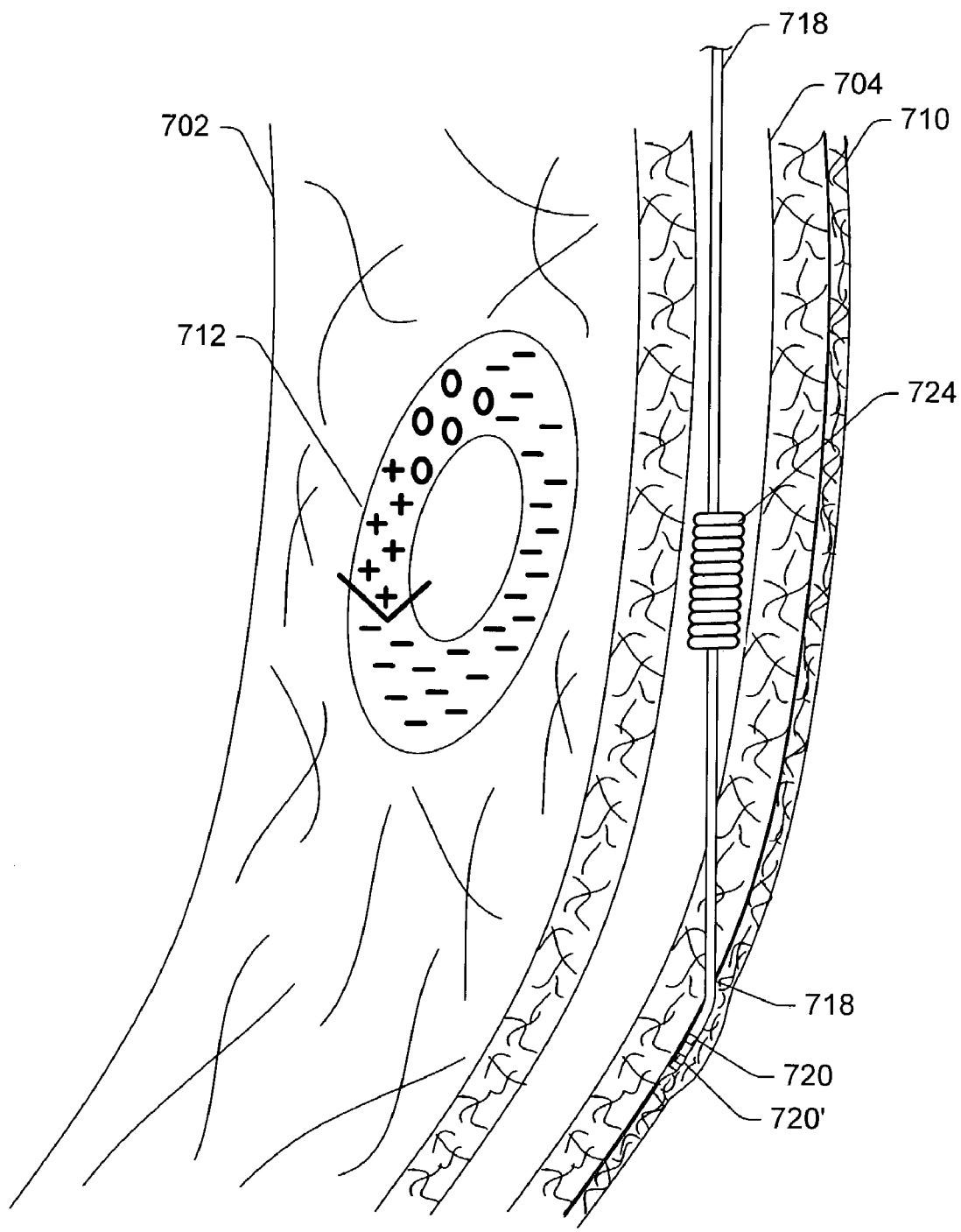
FIG. 13 is an approximate anatomical diagram of a cross-section of a human heart, a re-entrant pathway and a stimulation lead.

Referring to FIG. 13, a simplified approximate anatomical diagram of a cross-section of a heart is shown. From left to right, the diagram includes a cross-section through a heart wall 702, a cross-section through a vein 704 and a cross-section through the pericardium 710. A lead 718 having a large electrode 724 and two smaller distal electrodes 720, 720' are also shown. Note that the distal electrodes 720, 720' are positioned exteriorly of the vein 704, between the vein wall 704 and the pericardium 710.

Also shown in FIG. 13, within the heart wall 702 is a re-entrant pathway or circuit 712. As shown, the re-entrant pathway 712 surrounds a core, which is typically inactive scar tissue. The re-entrant pathway 712 includes a depolarization front marked by an arrowhead having positive charges on one side and negative charges on the other side. The positive charges represent depolarized tissue while the negative charges represent tissue at and/or near a rest potential and/or at a negative potential capable of depolarization. As mentioned in the Background section, such tissue may be referred to as the "excitable gap". As shown in FIG. 13, the depolarization front, and corresponding excitable gap, travel in a counter-clockwise direction. Further, while not explicitly shown, the depolarization front may trigger depolarization of tissue surrounding the re-entrant pathway 712 and hence cause depolarization of a substantial region of heart tissue. In general, a goal of antitachycardia pacing is to disrupt the re-entrant pathway and thereby eliminate any resultant undesirable depolarization of heart tissue. As described herein, an exemplary method and/or device delivers a stimulus to a parasympathetic nerve to cause release of acetylcholine and a corresponding lengthening of an excitable gap. Following such a delivery, an intrinsic and/or extrinsic stimulus may excite the lengthened excitable gap and thereby disrupt the reentrant circuit.

An exemplary method for disrupting the re-entrant pathway includes delivering one or more stimulation pulses to one or more of the distal electrodes 720, 720' to stimulate a parasympathetic nerve and thereby cause release of acetylcholine in a region proximate to the re-entrant pathway 712. Further, after and/or during the delivery of such a pulse or pulses, one or more pacing pulses are administered, for example, using the coil electrode 724 and at least one other electrode, e.g., ring, tip, can, etc. For example, after delivery of one or more stimulation pulses using the distal electrodes 720, 720' in a bipolar fashion, then a stimulation device delivers one or more pacing pulses using one or more of the distal electrodes 720, 720' and the coil electrode 724 in a bipolar fashion (e.g., from distal electrodes 720, 720' to coil electrode 724).

Various exemplary methods optionally include positioning one or more electrodes in the superior vena cava (SVC), the inferior vena cava (IVC) and/or the coronary sinus (CS). Other sites may include jugular veins or other veins proximate to parasympathetic nerves or pressure sensors that can trigger parasympathetic responses. Various exemplary methods optionally include positioning one or more electrode in the azygous vein. Suitable electrode portions for positioning electrodes in or near a nerve and/or the heart include, but are not limited to, basket type or double helix type of electrode portions, see, e.g., U.S. patent application having Ser. No. 10/321,307, filed Dec. 16, 2002, entitled "Implantable lead and electrode portion", to Helland and Shelchuk, which is incorporated by referenced herein, and U.S. patent application having Ser. No. 10/000,333, filed Oct. 22, 2001, entitled "Implantable lead and method for stimulation the vagus nerve", to Weinberg, which is incorporated by reference herein.

In various exemplary methods, parasympathetic stimulation aims to stimulate a parasympathetic nerve and to avoid producing an evoked response from the myocardium. In this regard, parasympathetic stimulation may occur according to a power, frequency, duty cycle, phase (e.g., monophasic, biphasic, triphasic, etc.) that reduces the risk of myocardial stimulation and/or parasympathetic stimulation may occur during a refractory period of the myocardium to reduce the risk of myocardial stimulation.

Determining Vagal Tone and/or Inspiration/Postinspiration

Figure 14:
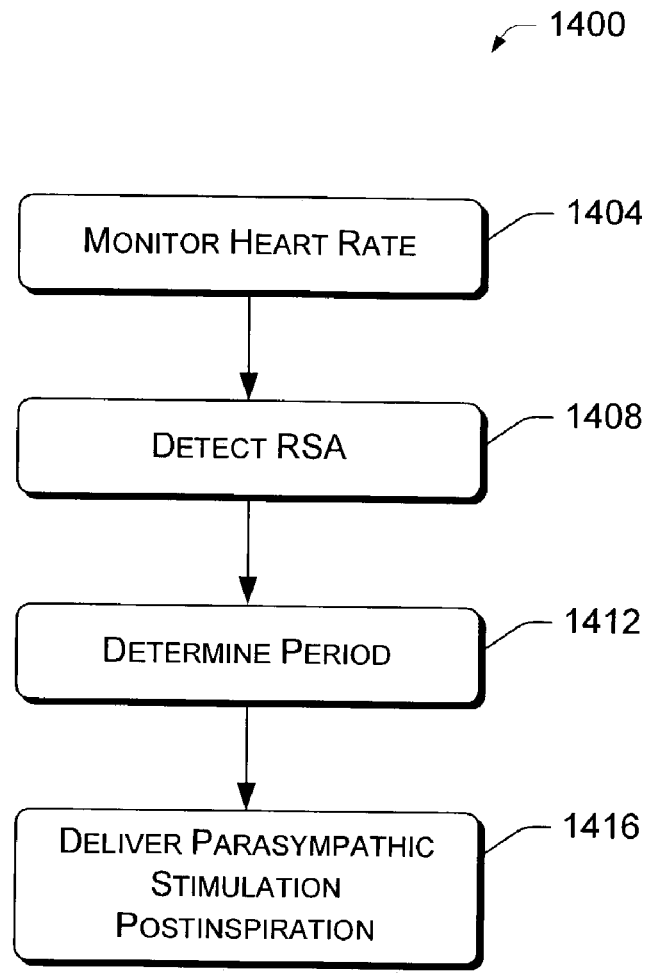
FIG. 14 is a block diagram of an exemplary method for delivering a stimulation pulse postinspiration.

As already mentioned, Mendelowitz noted that "cardiac vagal neurons recorded in vivo receive inhibitory synaptic input during inspiration, which is then followed by a rapid depolarization caused by excitatory synaptic input during postinspiration". Therefore, for a variety of reasons, the aforementioned exemplary methods and/or device optionally stimulate parasympathetic nerves postinspiration, i.e., not during inspiration. Referring to FIG. 14, an exemplary method 1400 for delivery of one or more stimulation pulses postinspiration is shown. In a monitoring block 1404, a stimulation and/or other device monitors directly and/or indirectly heart rate. Next, in a detection block 1408, the stimulation and/or other device detects respiratory sinus arrhythmia. Following detection, in a determination block 1412, the stimulation and/or other device determines a period associated with inspiration. Next, in a delivery block 1416, the stimulation device delivers a stimulation pulse to a parasympathetic nerve. Also note that such a method can determine a patient's vagal tone.

In another exemplary method, a stimulation and/or other device monitors inspiration directly and/or indirectly through use of a ventilation module and/or sensor, for example, minute ventilation. In this exemplary method and the aforementioned method, parasympathetic stimulation pulse delivery during postinspiration only can decrease power demand on an implantable stimulation device. In yet another exemplary method, parasympathetic stimulation pulse delivery occurs during a refractory period to avoid stimulation of cardiac and/or other tissue. Of course, an exemplary combined method optionally includes delivery of a parasympathetic stimulation pulse postinspiration in a refractory period.

Parasympathetic Stimulation Postinspiration and/or Synchronous with Heart

Figure 15:
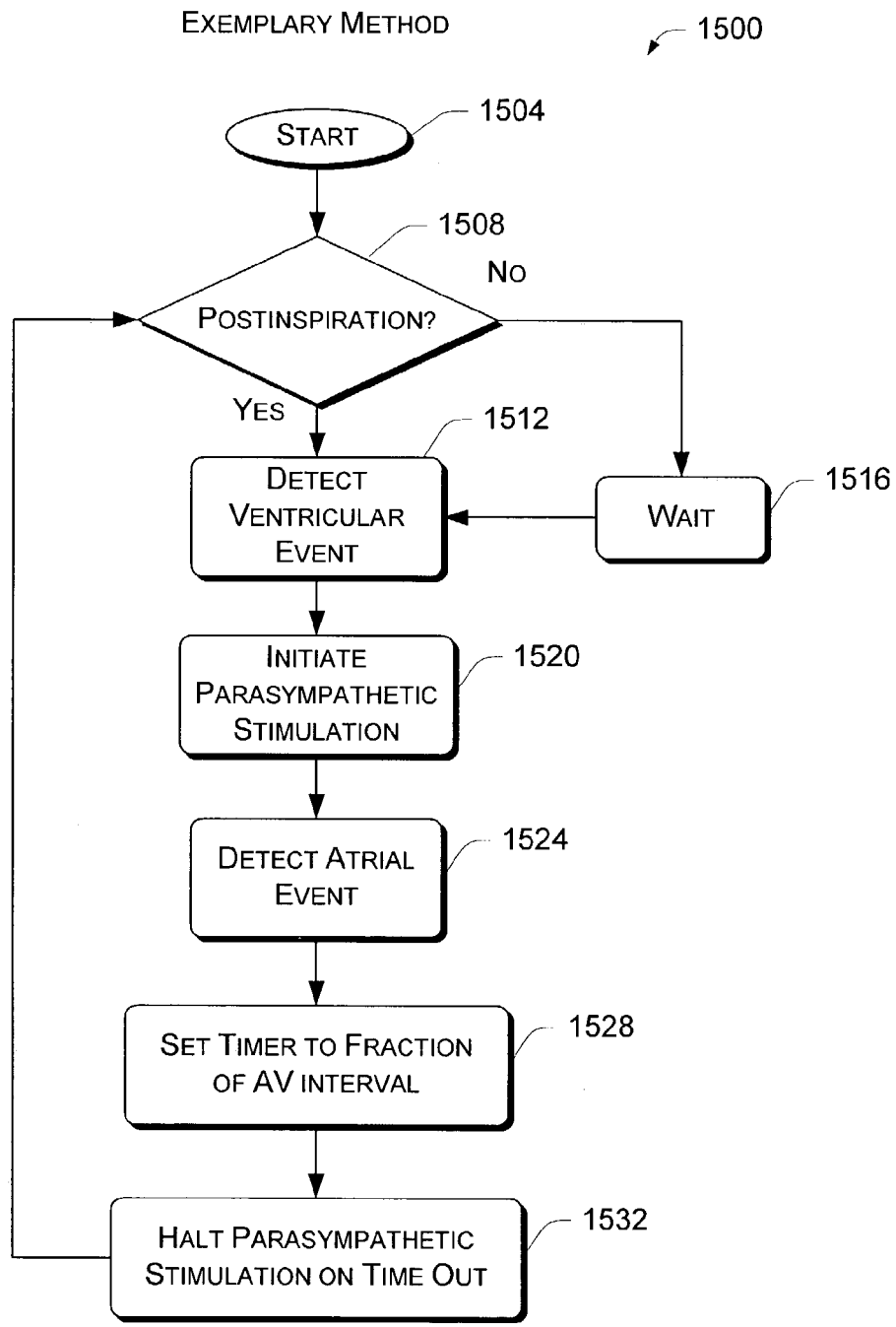
FIG. 15 is a block diagram of an exemplary method for delivering parasympathetic stimulation during a postinspiration phase and/or based on detection of one or more cardiac events

As already mentioned, parasympathetic stimulation may occur postinspiration (e.g., not during inspiration) and/or in synchrony with one or more cardiac events (e.g., events typically found in a cardiac cycle). FIG. 15 shows an exemplary method 1500 wherein parasympathetic stimulation occurs according to respiratory cycle and/or according to one or more events in a cardiac cycle. Various exemplary methods presented herein may implement one or more of the blocks or procedures described with reference to the exemplary method 1500.

A start block 1504 may occur at anytime an exemplary method desires to implement parasympathetic nerve stimulation. A decision block 1508 follows that determines whether a patient is in a postinspiration phase of a respiratory cycle. For example, an exemplary device may detect impedance, movement of an implanted device, pressure, cardiac characteristics, autonomic tone, etc., and then use such information to determine one or more phases of a respiratory cycle. In the exemplary method 1500, if the decision block 1508 determines that a patient is not in a postinspiration phase, then the method 1500 may continue in a wait block 1516, which either causes an appropriate delay or waits for an event indicative of a postinspiration phase. If the decision block 1508 determines that a patient is in a postinspiration phase, the method 1500 continues in a ventricular event detection block 1512; the wait block 1516 also continues at the ventricular event detection block 1512. In general, the ventricular event detection block 1512 aims to detect an R wave or a ventricular contraction. As described above, parasympathetic stimulation may act to terminate an SVA.

Upon detection of a particular event, the method 1500 then initiates parasympathetic stimulation in an initiation block 1520. The stimulation may continue for a set period of time, may continue until detection of another cardiac event or may continue for a certain amount of time based on detection of a subsequent cardiac event. As shown in FIG. 15, the method 1500 includes an atrial event detection block 1524. For example, such a detection block may detect an atrial paced event and/or an intrinsic atrial event, even an event related to an SVA. Upon detection of the atrial event, the method 1500 proceeds to set a timer to a fraction of an atrioventricular interval or other suitable interval in a set timer block 1528. Upon expiration of the timer, a halt parasympathetic stimulation block 1532 halts parasympathetic stimulation. In this example, parasympathetic stimulation may be halted to ensure that the parasympathetic stimulation does not cause any significant detriment to active contractility. Thereafter, the exemplary method 1500 continues at the decision block 1508, at the detection block 1512 or at another suitable point (e.g., a decision block that decides whether further parasympathetic stimulation is required). Of course, as mentioned above, parasympathetic stimulation may be delivered during a refractory period of the myocardium (e.g., the myocardium proximate to one or more electrodes). Hence, the exemplary method 1500 optionally includes stimulating during a refractory period, for example, to reduce the risk of producing an evoked response from the myocardium.

Ventricular Back-Up

Figure 16:
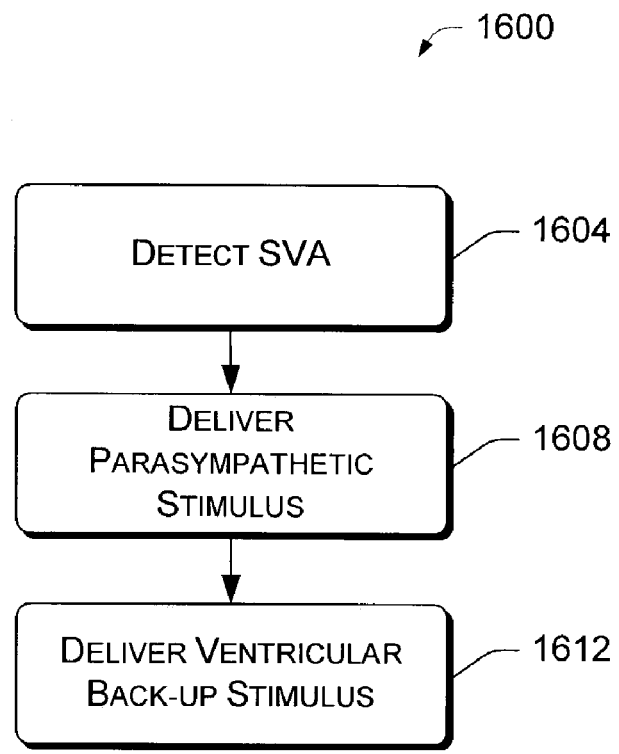
FIG. 16 is a block diagram of an exemplary method for optionally delivering a ventricular back-up stimulus.

FIG. 16 shows an exemplary method 1600 that optionally delivers a ventricular back-up stimulus. Depending on circumstances and parasympathetic stimulation parameters, parasympathetic stimulation may affect AV nodal conduction. In particular, parasympathetic stimulation may slow AV nodal conduction and/or effectively block AV nodal conduction (e.g., typically temporarily). Thus, the exemplary method 1600 optionally delivers a ventricular back-up pulse where parasympathetic stimulation significantly slows, blocks, or is at risk of significantly slowing or blocking AV nodal conduction. The exemplary method 1600 commences in a detection block 1604, which detects an SVA. Once the SVA has been detected, a delivery block 1608 delivers parasympathetic stimulation (e.g., afferent or efferent). Next, another delivery block 1612 delivers a ventricular back-up stimulus to compensate for impaired AV nodal conduction.

Selecting and/or Positioning Leads and/or Electrodes

An exemplary method for selecting and/or positioning a lead and/or an electrode is optionally implemented during implantation and/or after implantation. For example, during an implantation procedure, a patient is optionally instrumented to monitor heart function. For example, heart rate may be monitored via an EKG and contractility via arterial pressure sensors (e.g., the time derivative of the pressure can provide a good measure of contractility). In this example, monitoring of cardiac function and/or other functions may occur through use of external instrumentation and/or through use of implanted leads and/or sensors.

Consider a situation wherein parasympathetic tuning via parasympathetic nerve stimulation aims to decrease heart rate, to increase end diastolic volume and/or to decrease AV conduction. In such a situation, an exemplary method includes adjusting pulse amplitude and/or pulse frequency to relatively high values, automatically or manually (e.g., an implantable device having a lead and/or electrode implantation, selection and/or positioning mode(s)). In this exemplary method, through use of stimulation pulses and monitoring of cardiac function and/or other functions, a lead and/or electrode is positioned during implantation to achieve an optimal and/or a satisfactory decrease in heart rate (e.g., an increase of therapeutic value), increase in end diastolic volume and/or decrease in AV conduction. In this exemplary method, for example, a physician may slowly move a lead throughout an appropriate region and deliver pulses until a desired decrease in heart rate, increase in end diastolic volume and/or decrease in AV conduction is seen maximally via monitoring.

In yet another exemplary method, a lead and/or an electrode are optionally positioned to decrease sympathetic activity while at the same time minimizing stimulation effects on heart rate. Once a "sweet spot" is found, then pulse parameters are optionally adjusted to minimize electrical power consumption, for example, by previously mentioned exemplary methods.

Conjunct to Sympathomimetics

Sympathomimetic drugs such as dobutamine and angiotensin II are known to increase heart rate and contractility (positive inotropic therapy), see, e.g., Levett et al., "Cardiac augmentation can be maintained by continuous exposure of intrinsic cardiac neurons to a beta-adrenergic agonist or angiotensin II", *J. Surg. Res.*, 66(2): 167–173 (1996). However, according to Burger et al., "Comparison of the occurrence of ventricular arrhythmias in patients with acutely decompensated congestive heart failure receiving dobutamine versus nesiritide therapy", *Am. J. Cardiol.*, 88(1):

35–39 (2001), ventricular arrhythmias, which are common in patients with congestive heart failure (CHF), may be exacerbated by positive inotropic therapy. Thus, various exemplary methods and/or stimulation devices presented herein may be implemented in conjunction with administration of inotropic agents. For example, stimulation of efferent parasympathetic nerves may release acetylcholine, which has an anti arrhythmic effect, i.e., reduces the risk of arrhythmia.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method comprising:
   detecting a supraventricular arrhythmia;
   providing an electrode portion of a lead extending through a wall of a great cardiac vein and along nerves emanating from a ventral right atrial subplexus;
   stimulating at a vessel emanating from an epicardial subplexus according to one or more stimulation parameters using the electrode portion;
   determining whether the supraventricular arrhythmia terminated, became more complex or became less complex;
   halting the stimulating if the supraventricular arrhythmia terminated;
   halting the stimulating if the supraventricular arrhythmia became more complex; and
   repeating the stimulating if the supraventricular arrhythmia became less complex.

2. The method of claim 1, further comprising adjusting one or more of the one or more stimulation parameters based at least in part on the determining.

3. The method of claim 2, wherein the adjusting adjusts the one or more of the one or more stimulation parameters to change stimulation power.

4. The method of claim 2, wherein the adjusting adjusts the one or more of the one or more stimulation parameters to ramp down stimulation power with respect to time.

5. The method of claim 1, wherein the determining includes determining if amplitude of an atrial activity signal increased.

6. The method of claim 1, wherein the determining includes determining if an atrial signal is substantially periodic.

7. The method of claim 1, wherein the determining relies at least in part on a ventricular activity signal.

8. The method of claim 1, further comprising delivering one or more stimuli to a ventricle.

9. The method of claim 1, further comprising delivering one or more stimuli to an atrium.

10. The method of claim 1, wherein the stimulating occurs postinspiration.

11. The method of claim 1, wherein the stimulating occurs during diastole.

12. The method of claim 1, wherein the stimulating is synchronized to one or more cardiac events.

13. The method of claim 1, wherein the stimulating is synchronized to one or more respiratory events.

14. A method comprising:
    detecting a supraventricular arrhythmia;
    providing an electrode portion of a lead extending through a wall of a great cardiac vein and along nerves emanating from a left dorsal subplexus;
    stimulating at a vessel emanating from an epicardial subplexus according to one or more stimulation parameters using the electrode portion;
    determining whether the supraventricular arrhythmia terminated, became more complex or became less complex;
    halting the stimulating if the supraventricular arrhythmia terminated;
    halting the stimulating if the supraventricular arrhythmia became more complex; and
    repeating the stimulating if the supraventricular arrhythmia became less complex.

15. The method of claim 14, further comprising adjusting one or more of the one or more stimulation parameters based at least in part on the determining.

16. The method of claim 15, wherein the adjusting adjusts the one or more of the one or more stimulation parameters to change stimulation power.

17. The method of claim 15, wherein the adjusting adjusts the one or more of the one or more stimulation parameters to ramp down stimulation power with respect to time.

18. The method of claim 14, wherein the determining includes determining if amplitude of an atrial activity signal increased.

19. The method of claim 14, wherein the determining includes determining if an atrial signal is substantially periodic.

20. The method of claim 14, wherein the determining relies at least in part on a ventricular activity signal.

21. The method of claim 14, further comprising delivering one or more stimuli to a ventricle.

22. The method of claim 14, further comprising delivering one or more stimuli to an atrium.

23. The method of claim 14, wherein the stimulating occurs during diastole.

24. The method of claim 14, wherein the stimulating is synchronized to one or more cardiac events.

25. The method of claim 14, wherein the stimulating is synchronized to one or more respiratory events.

26. A method comprising:
    detecting a supraventricular arrhythmia;
    providing an electrode portion of a lead extending through a wall of a superior vena cava and along nerves emanating from at least one of the group comprising a ventral right atrial subplexus and a dorsal right atrial subplexus;
    stimulating at a vessel emanating from an epicardial subplexus according to one or more stimulation parameters using the electrode portion;
    determining whether the supraventricular arrhythmia terminated, became more complex or became less complex;
    halting the stimulating if the supraventricular arrhythmia terminated;
    halting the stimulating if the supraventricular arrhythmia became more complex; and
    repeating the stimulating if the supraventricular arrhythmia became less complex.

27. The method of claim 26, further comprising adjusting one or more of the one or more stimulation parameters based at least in part on the determining.

28. The method of claim 27, wherein the adjusting adjusts the one or more of the one or more stimulation parameters to change stimulation power.

29. The method of claim 27, wherein the adjusting adjusts the one or more of the one or more stimulation parameters to ramp down stimulation power with respect to time.

30. The method of claim 26, wherein the determining includes determining if amplitude of an atrial activity signal increased.

31. The method of claim 26, wherein the determining includes determining if an atrial signal is substantially periodic.

32. The method of claim 26, wherein the determining relies at least in part on a ventricular activity signal.

33. The method of claim 26, further comprising delivering one or more stimuli to a ventricle.

34. The method of claim 26, further comprising delivering one or more stimuli to an atrium.

35. The method of claim 26, wherein the stimulating occurs during diastole.

36. The method of claim 26, wherein the stimulating is synchronized to one or more cardiac events.

37. The method of claim 26, wherein the stimulating is synchronized to one or more respiratory events.

* * * * *